United States Patent
Gruenbacher et al.

(10) Patent No.: US 10,806,816 B2
(45) Date of Patent: Oct. 20, 2020

(54) MICROFLUIDIC CARTRIDGE AND MICROFLUIDIC DELIVERY DEVICE COMPRISING THE SAME

(71) Applicant: The Procter & Gamble Company, Cincinnati, OH (US)

(72) Inventors: Dana Paul Gruenbacher, Fairfield, OH (US); William Michael Cannon, West Harrison, OH (US); Hua Hu, Mason, OH (US); James Thomas Sullivan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 302 days.

(21) Appl. No.: 15/979,510

(22) Filed: May 15, 2018

(65) Prior Publication Data

US 2019/0351088 A1 Nov. 21, 2019

(51) Int. Cl.
*A61L 9/12* (2006.01)

(52) U.S. Cl.
CPC ......... *A61L 9/122* (2013.01); *A61L 2209/133* (2013.01)

(58) Field of Classification Search
CPC .......................... A61L 9/122; A61L 2209/133
See application file for complete search history.

(56) References Cited

U.S. PATENT DOCUMENTS

| | | |
|---|---|---|
| 7,669,978 B2 | 3/2010 | Spivey et al. |
| 7,938,974 B2 | 5/2011 | McAvoy et al. |
| 8,020,573 B2 | 9/2011 | Lamers et al. |
| 8,087,759 B2 | 1/2012 | Oikawa et al. |
| 8,109,609 B2 | 2/2012 | Shim et al. |
| 8,142,558 B2 | 3/2012 | Robertson et al. |
| 8,201,752 B2 | 6/2012 | Brodbeck et al. |
| 8,251,500 B2 | 8/2012 | Yamada et al. |
| 8,338,346 B2 | 12/2012 | Diersing et al. |
| 8,430,484 B2 | 4/2013 | Fang |
| 8,821,802 B2 | 9/2014 | Haran |

(Continued)

FOREIGN PATENT DOCUMENTS

| | | |
|---|---|---|
| CA | 2213066 A1 | 2/1999 |
| CN | 1393491 A | 1/2003 |

(Continued)

OTHER PUBLICATIONS

Search Report; Serial No. PCT/US2019/031004; dated Jul. 30, 2019; 16 Pages.

(Continued)

*Primary Examiner* — Sean E Conley
(74) *Attorney, Agent, or Firm* — Abbey A. Lopez

(57) ABSTRACT

A microfluidic delivery device and method of dispensing a fluid composition from a microfluidic die are provided. The method includes generating air flow from a fan; directing a first portion of the air flow through a first air outlet in a housing; directing a second portion of the air flow through a second air outlet in the housing; jetting a fluid composition from a microfluidic die through a fluid orifice in the housing; directing the second portion of air flow adjacent to the microfluidic die and out the fluid outlet, wherein the first portion of the air flow directs the fluid composition jetted out of the fluid outlet into the air.

8 Claims, 20 Drawing Sheets

(56) References Cited

U.S. PATENT DOCUMENTS

| | | | |
|---|---|---|---|
| 8,870,090 | B2 | 10/2014 | Feriani et al. |
| 8,881,999 | B2 | 11/2014 | Blaylock et al. |
| 9,174,453 | B1 | 11/2015 | Dodd et al. |
| 9,211,356 | B2 | 12/2015 | Gruenbacher et al. |
| 9,211,980 | B1 | 12/2015 | Gruenbacher et al. |
| 9,377,786 | B2 | 6/2016 | Nakamoto et al. |
| 9,554,459 | B2 | 1/2017 | Gruenbacher et al. |
| 9,636,430 | B2 | 5/2017 | Gruenbacher et al. |
| 2015/0367014 | A1 | 12/2015 | Gruenbacher |
| 2016/0081181 | A1* | 3/2016 | Gruenbacher ....... H05B 1/0244 392/387 |
| 2017/0072084 | A1 | 3/2017 | Gruenbacher |
| 2019/0117816 | A1 | 4/2019 | Dycher |
| 2019/0117817 | A1 | 4/2019 | Dycher |
| 2019/0117818 | A1 | 4/2019 | Dycher |

FOREIGN PATENT DOCUMENTS

| | | |
|---|---|---|
| CN | 1223637 | 10/2005 |
| CN | 101020073 | 8/2007 |
| CN | 204072869 | 1/2015 |
| EA | 2143576 | 11/2012 |
| EP | 1510228 A1 | 3/2005 |
| EP | 1022063 B1 | 12/2007 |
| EP | 1894727 A3 | 10/2009 |
| EP | 2841208 A1 | 3/2015 |
| GB | 2410468 B | 9/2008 |
| JP | H09123453 A | 5/1997 |
| JP | 2002254613 A | 9/2002 |
| JP | 2004311093 | 11/2004 |
| JP | 2005185366 | 7/2005 |
| JP | 2008168223 | 7/2005 |
| JP | 2005224503 A | 8/2005 |
| JP | 2005224504 | 8/2005 |
| JP | 2007054446 | 3/2007 |
| JP | 2008061937 | 3/2008 |
| JP | 2009213901 | 9/2009 |
| KR | 100238582 | 1/2000 |
| WO | WO0130404 A1 | 5/2001 |
| WO | WO0232470 A1 | 4/2002 |
| WO | WO200444552 A2 | 5/2004 |
| WO | WO200604902 A1 | 1/2006 |
| WO | WO2007083164 A3 | 10/2007 |
| WO | WO2009064453 A1 | 5/2009 |
| WO | WO2011021980 A1 | 2/2011 |
| WO | WO2014043424 A1 | 3/2014 |
| WO | WO2015195994 A1 | 12/2015 |
| WO | WO2015175527 A4 | 5/2016 |
| WO | WO2017215726 A1 | 12/2017 |
| WO | WO2017215727 A1 | 12/2017 |
| WO | WO2017215728 A1 | 12/2017 |

OTHER PUBLICATIONS

U.S. Appl. No. 15/936,469, filed Mar. 27, 2018, Gruenbacher, et al.
U.S. Appl. No. 15/936,471, filed Mar. 27, 2018, Gruenbacher, et al.
U.S. Appl. No. 15/936,474, filed Mar. 27, 2018, Gruenbacher, et al.
U.S. Appl. No. 15/936,477, filed Mar. 27, 2018, Gruenbacher, et al.
U.S. Appl. No. 15/939,348, filed Mar. 29, 2018, Lane, et al.
U.S. Appl. No. 16/005,781, filed Jun. 12, 2018, Gruenbacher, et al.

* cited by examiner

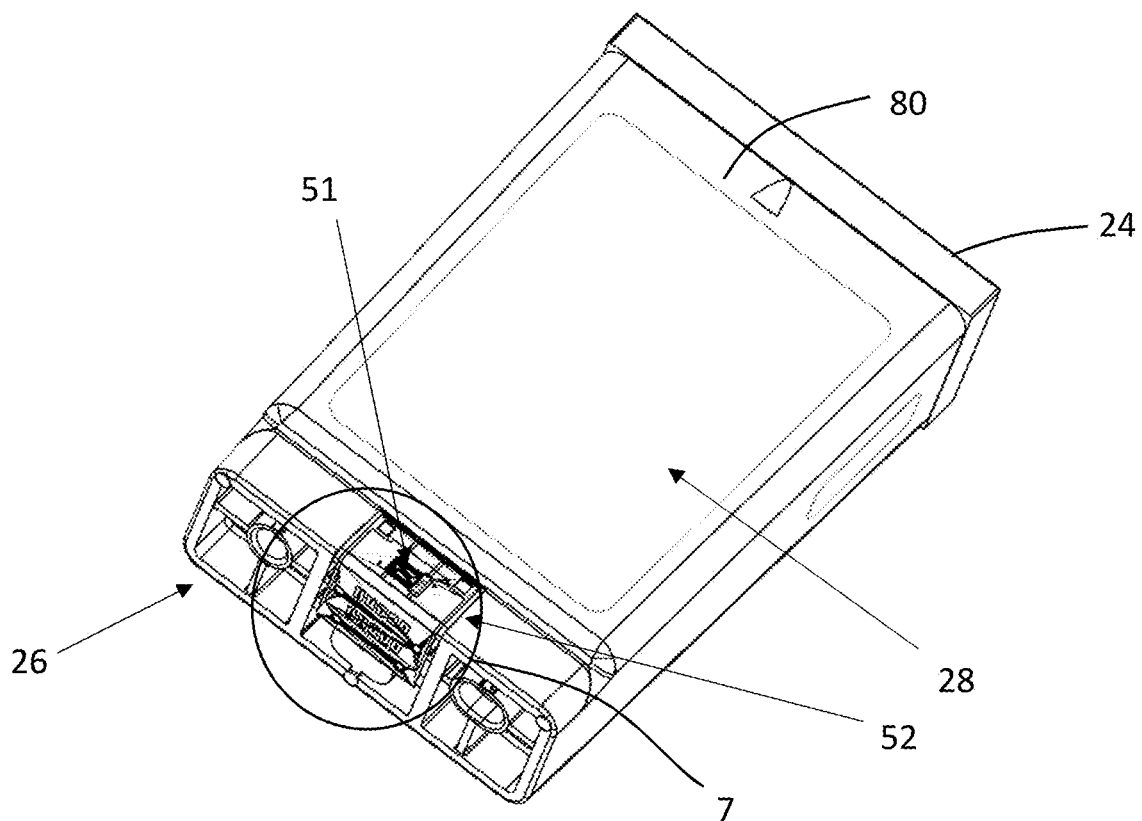
Fig. 6
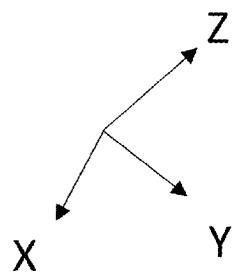

MICROFLUIDIC CARTRIDGE AND MICROFLUIDIC DELIVERY DEVICE COMPRISING THE SAME

FIELD

The present disclosure is directed to a microfluidic delivery device having a microfluidic die for dispensing a fluid composition into the air.

BACKGROUND

Microfluidic cartridges exist for delivering compositions either onto a surface or into the air. Microfluidic cartridges may contain a fluid composition, a microfluidic die, and one or more nozzles for dispensing the fluid composition. The microfluidic cartridges may be releasably connectable with a microfluidic delivery device that may include, for example, a housing having electrical connections that are in electrical communication with a power source. The fluid composition dispenses from the microfluidic die in the form of droplets. Some droplets may break into smaller droplets upon ejection from the microfluidic die or some droplets may form a tail portion that breaks away from the main portion of the droplet. These small droplets or tail portions of the droplets may in some instances fall back onto the microfluidic die, causing fluid composition to accumulate on the microfluidic die and potentially block some or all of the nozzles.

Therefore, there is a need to develop a microfluidic delivery device that is capable of propelling a fluid composition dispensed from a microfluidic die into the air so that it does not deposit back onto a microfluidic die.

SUMMARY

"Combinations:"
A. A microfluidic delivery device comprising:
a fan;
a housing having an interior and an exterior, the housing further comprising a first air outlet and a fluid outlet, the interior of the housing comprising an air flow channel that extends from the fan to the first air outlet, the first air outlet being open to the exterior of the housing, wherein the air flow channel comprises a second air outlet that is exposed to the interior of the housing and that is in air flow communication with the fluid outlet, wherein the housing further comprising housing electrical contacts in electrical connection with a power source;
a microfluidic cartridge releasably connectable with the housing, the microfluidic cartridge comprising:
a reservoir for containing a fluid composition;
an electrical circuit comprising a first end portion and a second end portion, wherein the first end portion of the electrical circuit is disposed on the first face and the second end portion of the electrical circuit is disposed on the second face; and
a microfluidic die disposed on the second face, wherein the microfluidic die is in electrical communication with the electrical circuit and in fluid communication with the reservoir, wherein the second air flow outlet is in air flow communication with the microfluidic die, wherein fluid composition dispensed from the microfluidic die exits the housing through the fluid outlet.
B. The microfluidic delivery device of Paragraph A, wherein air flow from the fan is directed through the first and second air outlets, wherein air flow entering the second air outlet travels adjacent to the microfluidic die and out of the fluid outlet along with the fluid composition.
C. The microfluidic delivery device of Paragraph A or Paragraph B, wherein the housing comprises a fluid channel extending from the fluid outlet toward the microfluidic die.
D. The microfluidic delivery device of any of Paragraphs A through C, wherein the air flow exiting the first air outlet travels at an upward angle relative to horizontal.
E. The microfluidic delivery device of any of Paragraphs A through D, wherein a majority of the air flow exits the first air outlet.
F. The microfluidic delivery device of any of Paragraphs A through E, wherein the fluid composition is dispensed substantially horizontal.
G. The microfluidic delivery device of any of Paragraphs A through F, wherein the microfluidic die comprises a semiconductor substrate comprising a plurality of thermal ejection actuators, a fluid flow substrate comprising a fluid supply channel and one or more fluid chambers, wherein each fluid chamber is associated with a fluid ejection actuator, and a nozzle plate comprising one or more nozzles, wherein each nozzle is in fluid communication with a fluid chamber, and wherein the fluid composition comprises a perfume mixture.
H. A method of dispensing a fluid composition from a microfluidic die, the method comprising the steps of:
generating air flow from a fan;
directing a first portion of the air flow through a first air outlet in a housing;
directing a second portion of the air flow through a second air outlet in the housing;
jetting a fluid composition from a microfluidic die through a fluid orifice in the housing;
directing the second portion of air flow adjacent to the microfluidic die and out the fluid outlet, wherein the first portion of the air flow directs the fluid composition jetted out of the fluid outlet into the air.
I. The method of Paragraph H, wherein the housing comprises an interior and an exterior, wherein the first air outlet opens up to the exterior of the housing, and wherein the second air outlet opens up to the interior of the housing.
J. The method of Paragraph I, wherein the housing comprises an air flow channel air flow that extends from the fan to the first air outlet, wherein the air flow channel comprises the second air outlet.
K. The method of Paragraph I or Paragraph J, wherein the housing comprises a fluid channel extending from the fluid outlet toward the microfluidic die.
L. The method of any of Paragraphs H through K, wherein the air flow exiting the first air outlet travels at an upward angle relative to horizontal.
M. The method of any of Paragraphs H through L, wherein a majority of the air flow exits the first air outlet.
N. The method of any of Paragraphs H through M, wherein the fluid composition is jetted substantially horizontal from the microfluidic die.
O. The method of any of Paragraphs H through N, wherein the microfluidic die comprises a semiconductor substrate comprising a plurality of thermal actuators, a fluid flow substrate comprising a fluid supply channel and one or more fluid chambers, wherein each fluid chamber is associated with a fluid ejection actuator, and a nozzle plate comprising one or more nozzles, wherein each nozzle is in fluid communication with a fluid chamber, and wherein the fluid composition comprises a perfume mixture.

BRIEF DESCRIPTION OF THE DRAWINGS

FIG. 6 is a perspective view of a microfluidic cartridge with an electrical circuit and microfluidic die shown.

DETAILED DESCRIPTION

Figure 1:
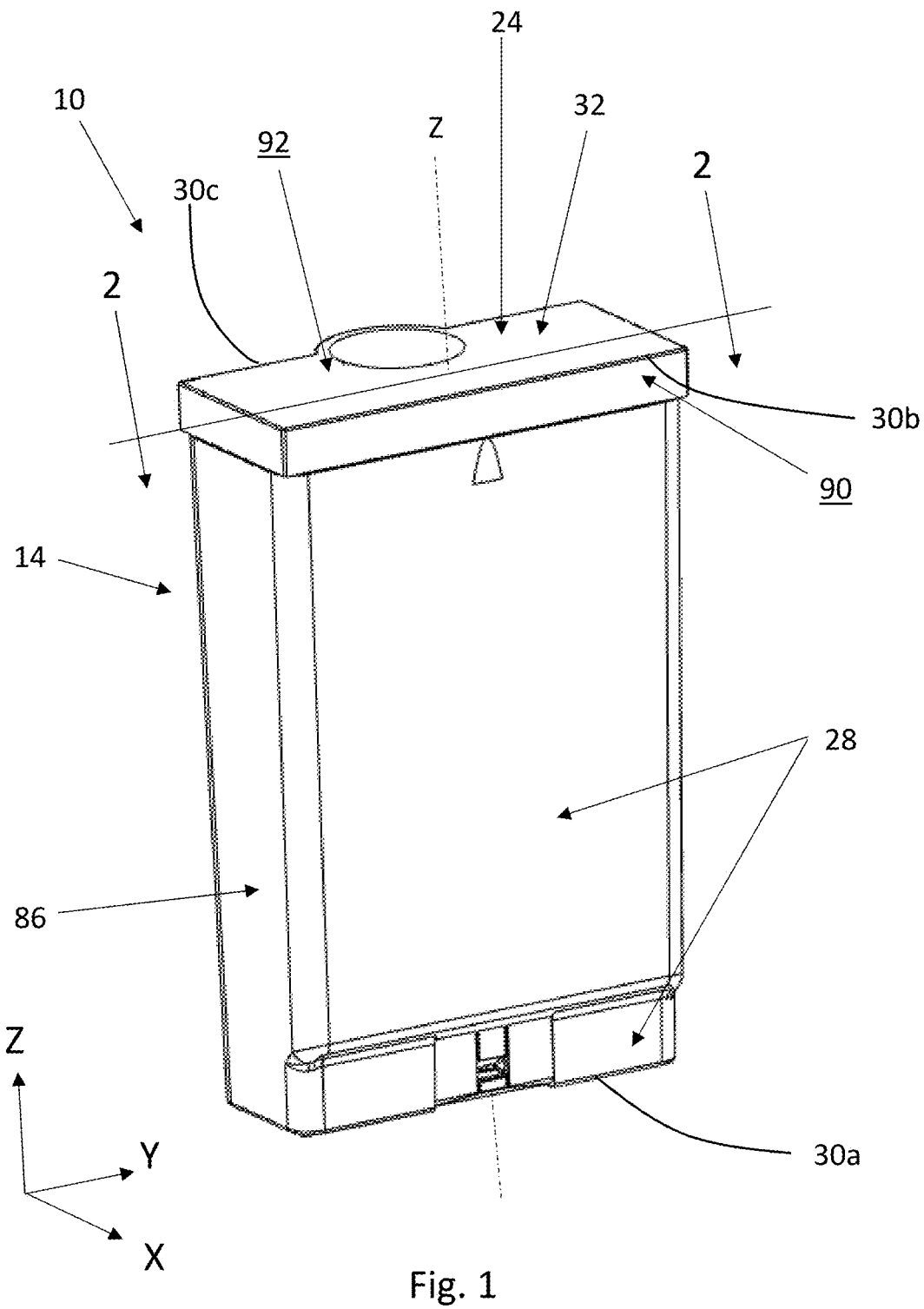
FIG. 1 is a perspective view of a microfluidic cartridge with an electrical circuit and microfluidic die removed to more clearly show details of the microfluidic cartridge.

While the below description describes a microfluidic cartridge and a microfluidic delivery device, both having various components, it is to be understood that the microfluidic cartridge and microfluidic delivery device are not limited to the construction and arrangement set forth in the following description or illustrated in the drawings. The microfluidic cartridge and microfluidic delivery device of the present disclosure are applicable to other configurations or may be practiced or carried out in various ways. For example, the microfluidic cartridge may be used with various devices or other housing configurations for delivering a fluid composition into the air.

Throughout the present disclosure, reference is made to cartesian coordinate system including an X-axis, Y-axis, and a Z-axis that extend from a common origin and that are mutually orthogonal. Reference may also be made to an X-direction, a Y-direction, and a Z-direction that run parallel with the respective axis. The microfluidic cartridge is configured to be connected with a microfluidic delivery device in a Z-direction.

The present disclosure is directed to a microfluidic cartridge. The microfluidic cartridge is configured to be releasably connectable with a microfluidic delivery device. The microfluidic cartridge may include an interior and an exterior. The interior of the microfluidic cartridge may comprise a reservoir for containing a liquid composition. The reservoir may include a fluid channel extending from reservoir and terminating at a fluid opening that is exposed to the exterior of the microfluidic cartridge.

The microfluidic cartridge may comprise three or more faces. For example, the microfluidic cartridge may comprise a top face, a bottom face that opposes the top face, and one or more side faces that extend between the top and bottom faces. Throughout the present disclosure, the microfluidic cartridge may be referred to as having a first face, a second face, a third face, etc. It is to be appreciated that the first face may be a bottom face, or a top face, or a side face, for example. Reference to numbered faces is provided only to discuss and distinguish features present on a single face that may not be present on another face, for example, and is not intended to limit the location or orientation of particular faces unless specifically defined as corresponding to a particular location or orientation.

The fluid opening may be disposed in a second face of the microfluidic cartridge. The microfluidic cartridge may include a microfluidic die disposed on the second face. The microfluidic die may be in fluid communication with the fluid opening.

A first face of the microfluidic cartridge may include one or more openings. The openings may properly align the microfluidic cartridge and limit movement of the microfluidic cartridge relative to a microfluidic delivery device. There may be more than one type of opening in the first face of the microfluidic cartridge. For example, the first face may include one or more minor openings and/or major openings. The major openings may assist a user with general alignment and orientation of the microfluidic cartridge with a microfluidic delivery device. The minor openings may provide for fine-tune alignment and stability with a microfluidic delivery device. In particular, the fine-tune alignment provided by the minor openings may assist with making a robust electrical connection with a microfluidic delivery device.

An electrical circuit may be disposed on the microfluidic cartridge to provide electricity to the microfluidic die. The electrical circuit may include a first end portion, a second end portion, and a central portion separating the first and second end portions. The first end portion of the electrical circuit may be disposed on the first face of the microfluidic cartridge, the second end portion of the electrical circuit may be disposed on the second end portion, and the central portion of the electrical circuit may span the first and second faces of the microfluidic cartridge. The first end portion of the electrical circuit may include electrical contacts for connecting with the electrical contacts of the housing of a microfluidic delivery device. The second end portion of the electrical circuit may provide electricity to the microfluidic die.

The first end portion of the electrical circuit may include one or more circuit openings. The circuit openings in the first end portion of the electrical circuit may align with the minor openings in the first face of the microfluidic cartridge, when present. If more than one circuit opening is present in the first end portion of the electrical circuit, at least two circuit openings may be disposed on opposite sides of the electrical contacts or may be separated by the electrical contacts in order to provide robust electrical connections. Circuit openings in the electrical circuit may also be present when minor openings are not present in the first face.

The microfluidic die includes delicate electrical components and micro-sized nozzles that can be easily clogged by debris or oils, for example. The microfluidic die may be disposed on the microfluidic cartridge such that it is protected from being damaged by being touched or hit by a user, hit against the housing of a microfluidic device, or hit against any other surface or object that the microfluidic cartridge may contact. For example, the second face of the microfluidic cartridge may be defined by a second face outermost point in the X-direction that extends furthest away from the X-axis from any other point on the second face. The microfluidic die may be disposed on a recessed region in the second face that is positioned inward in the X-direction from the second face outermost.

The microfluidic delivery device may comprise a housing and a power source. The housing may include a receptacle having an opening for receiving the microfluidic cartridge. The receptacle may receive a portion of the microfluidic cartridge or the microfluidic cartridge may be completely disposed within the receptacle. The receptacle of the housing may include electrical contacts that are in electrical connect with a power source and are configured to electrically connect with the electrical contacts of the microfluidic cartridge. The receptacle may include one or more minor guideposts and/or major guideposts that are received by the circuit openings, minor openings, and/or major openings, respectively.

The microfluidic cartridge may include one or more elements on a third face that assist the user with properly aligning the microfluidic cartridge into the housing. The third face may be a top face that may face a user as the user inserts the microfluidic cartridge into the housing. For example, the microfluidic cartridge may include one or a plurality of projections extending from the third face. The projection may align with a recessed region in the receptacle of the housing. The projection may extend in the X-direction to a third face outermost point. The projection may extend from the third face onto the fourth face such that the projection extends outward in the X-direction on the fourth face.

The microfluidic delivery device may include a fan for generating air flow to assist with delivering the fluid composition into the air. The fan may be used to push the fluid composition further into the air and/or may be used to direct the fluid composition in a different direction than the fluid composition is dispensed from the microfluidic die. The fan may be used to direct air over the microfluidic die to minimize the amount of fluid composition that is deposited back onto the microfluidic die.

Microfluidic Delivery Device

Figure 2:
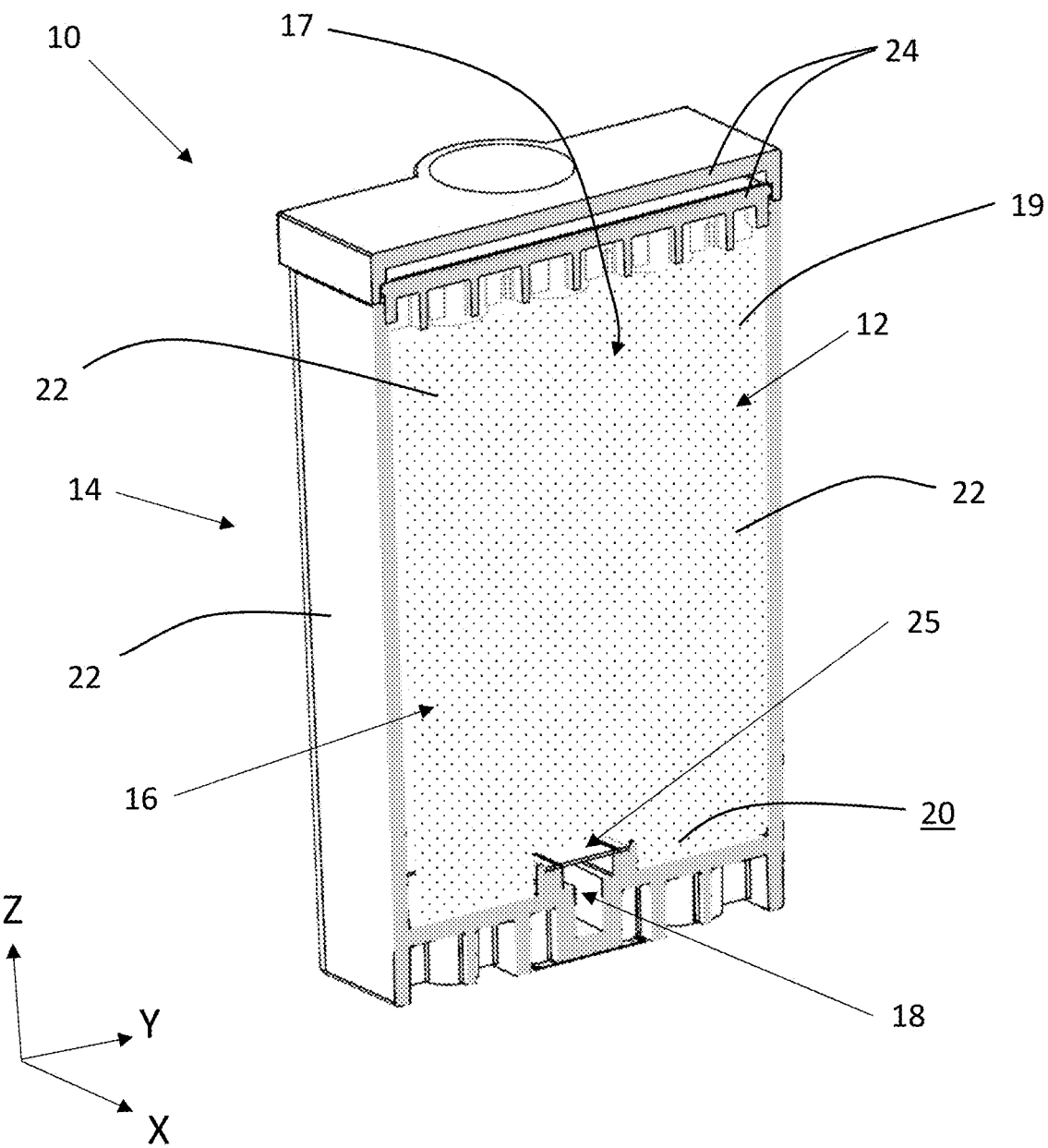
FIG. 2 is a sectional view of FIG. 1 taken along lines 2-2.
Figure 3:
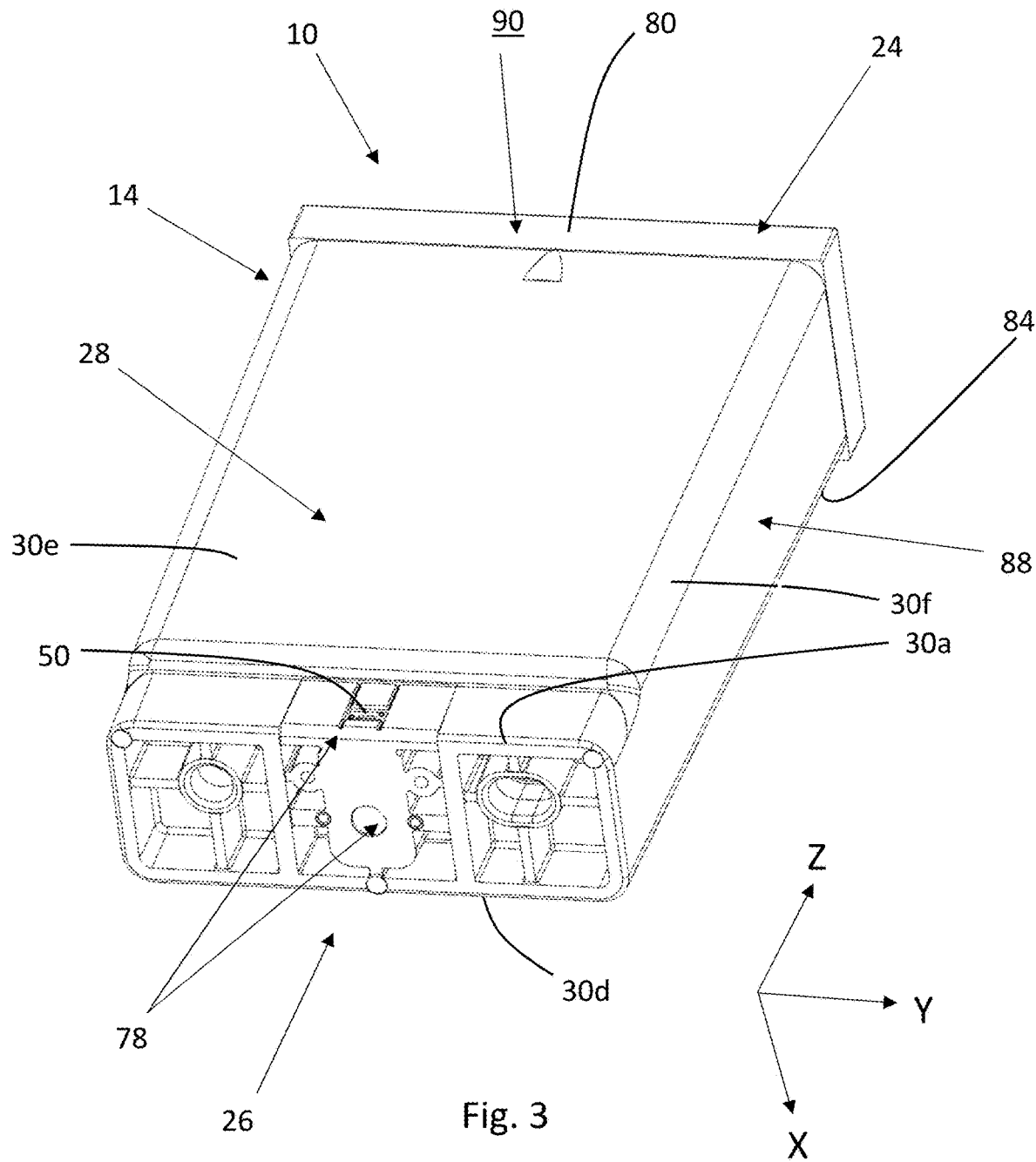
FIG. 3 is another perspective view of the microfluidic cartridge of FIG. 1.

With reference to FIGS. 1-3, a microfluidic cartridge 10 comprises an interior 12 and an exterior 14. The interior 12 of the microfluidic cartridge 10 comprises a reservoir 16 and one or more fluid channels 18. The reservoir 16 may be formed from a base wall 20 or a plurality of surfaces forming a base wall 20 and one or more side walls 22. The reservoir 16 may be enclosed by a lid 24 of the microfluidic cartridge 10. The fluid channel 18 extends from reservoir 16 to the exterior 14 of the microfluidic cartridge 10 at the fluid opening 50. The reservoir may include an air vent.

The reservoir 16 of the microfluidic cartridge 10 may contain from about 5 mL to about 50 mL of fluid composition, alternatively from about 10 mL to about 30 mL of fluid composition, alternatively from about 15 mL to about 20 mL of fluid composition. The reservoir 16 can be made of any suitable material for containing a fluid composition. Suitable materials for the containers include, but are not limited to, plastic, metal, ceramic, composite, and the like. A microfluidic cartridge may be configured to have multiple reservoirs, each containing the same or a different composition. The microfluidic delivery device may utilize one or more microfluidic cartridges, each containing a separate reservoir.

With reference to FIG. 2, the reservoir 16 may also contain a porous material 19 such as a sponge that creates a back pressure to prevent the fluid composition from leaking from the microfluidic die when the microfluidic die is not in operation. The fluid composition may travel through the porous material and to the microfluidic die through gravity force and/or capillary force acting on the fluid composition. The porous material may comprise a metal or fabric mesh, open-cell polymer foam, or fibrous polyethylene terephthalate, polypropylene, or bi-components of fibers or porous wick, that contain multiple interconnected open cells that form fluid passages. The porous material may comprise melamine foam. The porous material may be free of a polyurethane foam. The porous material is kept in intimate contact with a filter 25 attached to the top of fluid channel 18. The high capillary force generated by the filter maintains a fluid path between the porous material and fluid channel 18 while preventing air from entering the fluid channel. This intimate fluid connections also helps to maintain the negative pressure needed to contain the fluid inside the cartridge cavity 16 without leakage from the microfluidic die or the lid.

The lid 24 may be integral with the reservoir 16 or may be constructed as a separate element that is connected with the reservoir 16. The lid 24 may comprise one or more elements that are joined together or integrally formed as one component. The lid 24 may include a lid top surface 92 and one or more lid side surfaces 90. The lid 24 may be sized to match the size of the reservoir opening 17. Or, the lid may be larger than the reservoir opening 17 such that one or more lid side surfaces 90 extend further out on the respective face in the X or Y-directions than all or a portion of the sidewall 22 of the reservoir 16 extends.

With reference to FIGS. 1 and 3, the exterior 12 of the microfluidic cartridge 10 is made up of two, three, or more faces. Each face is bounded by one or more edges. Two faces are connected along an edge. Each face may be flat, substantially flat, or contoured in various ways. The faces may connect to form various shapes, such as a cube, cylinder, cone, tetrahedron, triangular prism, cuboid, etc. The microfluidic cartridge may be comprised of various materials, including plastic, metal, glass, ceramic, wood, composite, and combinations thereof. Different elements of the microfluidic cartridge may be comprised of the same or different materials.

With reference to FIGS. 1 and 3, the microfluidic cartridge 10 may comprise at least a first face 26 and a second face 28 joined along a first edge 30a. For example, the first face 26 may be a bottom face and the second face 28 may be a side face. The microfluidic cartridge 10 may comprise a third face 32, such as a top face for example, that substantially opposes the first face 26. The Z-axis may bisect the first and second faces 26 and 32, respectively. The second face 28 may be joined with the third face 32 along a second edge 30 b.

The microfluidic cartridge 10 may include one or more side faces. In a microfluidic cartridge 10 that is substantially cube-shaped, the microfluidic cartridge 10 may include a top face, a bottom face that opposes the top face, and four side faces extending between the top and bottom faces. Each joining face may be connected along an edge. In a cylindrical-shaped microfluidic cartridge, for example, the microfluidic cartridge may include a top face, a bottom face opposing the top face, and a single curved side face extending between the top and bottom faces.

With reference to FIGS. 1 and 3-5, the microfluidic cartridge 10 may include one or more side faces. For example, the microfluidic cartridge may include the second face 28, a fourth face 84 that opposes the second face 28, a fifth face 86 joined with the second face 28 and joining the first and third faces 28 and 32, a sixth face 88 joined with the second face 28 and opposing the fifth face 86. The fourth face 84 may be connected with the third face 32 at a third edge 30c and with the first face 26 at a fourth edge 30d.

With reference to FIGS. 2 and 3, the fluid channel 18 of the microfluidic cartridge 10 may extend to the fluid opening 50 that may be disposed in the second face 28 of the microfluidic cartridge 10. With reference to FIGS. 3-7, the microfluidic cartridge 10 may include a microfluidic die 51 disposed on the second face 28. The microfluidic die 51 may be in fluid communication with the fluid opening 50.

The primary components of a microfluidic die are a semiconductor substrate, a flow feature layer, and a nozzle plate layer. The flow feature layer and the nozzle plate layer may be formed from two separate layers or one continuous layer. The semiconductor substrate is preferably made of silicon and contains various passivation layers, conductive metal layers, resistive layers, insulative layers and protective layers deposited on a device surface thereof. Fluid ejection actuators in the semiconductor substrate generate rapid pressure impulses to eject the fluid composition from the nozzles. The rapid pressure impulses may be generated by piezoelectric device that vibrates at a high frequency (e.g., micro mechanical actuation) or by a heater resistor that cause volatilization of a portion of a fluid composition within the fluid composition through rapid heating cycles (e.g., micro thermal nucleation). For thermal actuators, individual heater resistors are defined in the resistive layers and each heater resistor corresponds to a nozzle in the nozzle plate for heating and ejecting the fluid composition from the nozzle.

Figure 8:
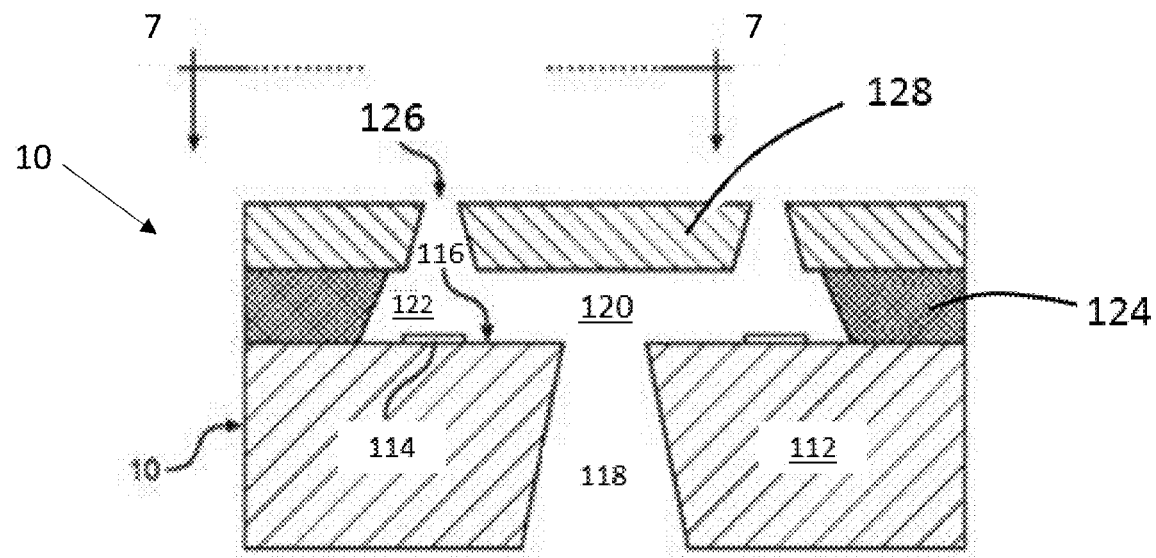
FIG. 8 is a sectional view of a microfluidic die.
Figure 9:
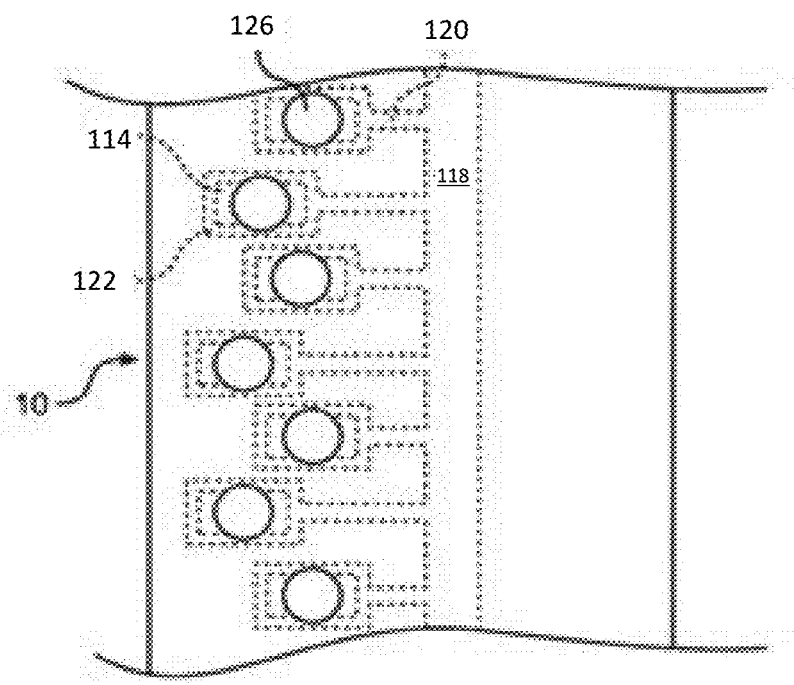
FIG. 9 is a plan view of a portion of a microfluidic die.
Figure 10:
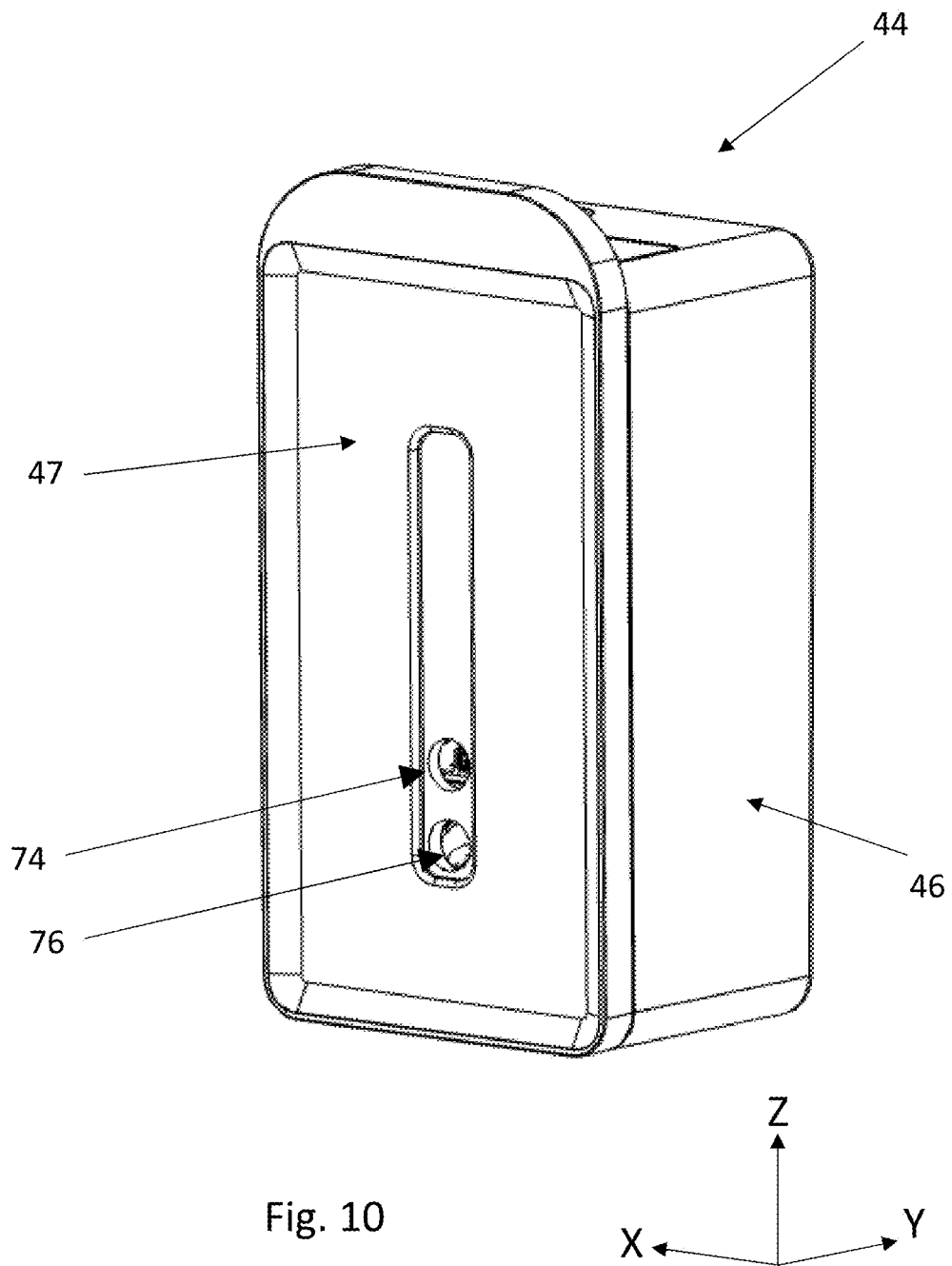
FIG. 10 is a perspective view of a microfluidic delivery device having a microfluidic cartridge releasably connected with a housing.

With reference to FIGS. 8 and 9, there is shown a simplified representation of a portion of a microfluidic die 10. The microfluidic die includes a semiconductor substrate 112 that may be a silicon semiconductor substrate 112 containing a plurality of fluid ejection actuators 114 such as piezoelectric devices or heater resistors formed on a device side 116 of the substrate 112 as shown in the simplified illustration of FIG. 9. In a microfluidic die having piezo actuators as the fluid ejection actuators 114, the piezo actuator may be disposed adjacent the nozzle such as shown in FIG. 9 or may be disposed away from the nozzles and still transmit the pressure pulse to the fluid composition to be ejected from the nozzles. Upon activation of fluid ejection actuators 114, fluid supplied through one or more fluid supply vias 118 in the semiconductor substrate 112 flows through a fluid supply channel 120 to a fluid chamber 122 in a thick film layer 124 where the fluid is caused to be ejected through nozzles 126 in a nozzle plate 128. Fluid ejection actuators are formed on the device side 116 of the semiconductor substrate 112 by well-known semiconductor manufacturing techniques. Thick film layer 124 and nozzle plate 128 may be separate layers or may be one continuous layer.

The nozzle plate 128 may include about 4-200 nozzles 126, or about 6-120 nozzles, or about 8-64 nozzles. Each nozzle 126 may deliver about 0.5 to about 35 picoliters, or about 1 to about 20 picoliters, or about 2 to about 10 picoliters of a fluid composition per electrical firing pulse. Individual nozzles 126 may have of a diameter typically about 0.0024 inches (5-50 microns). The flow rate of fluid composition released from the microfluidic die 51 could be in the range of about 5 to about 70 mg/hour or any other suitable rate or range.

Figure 4:
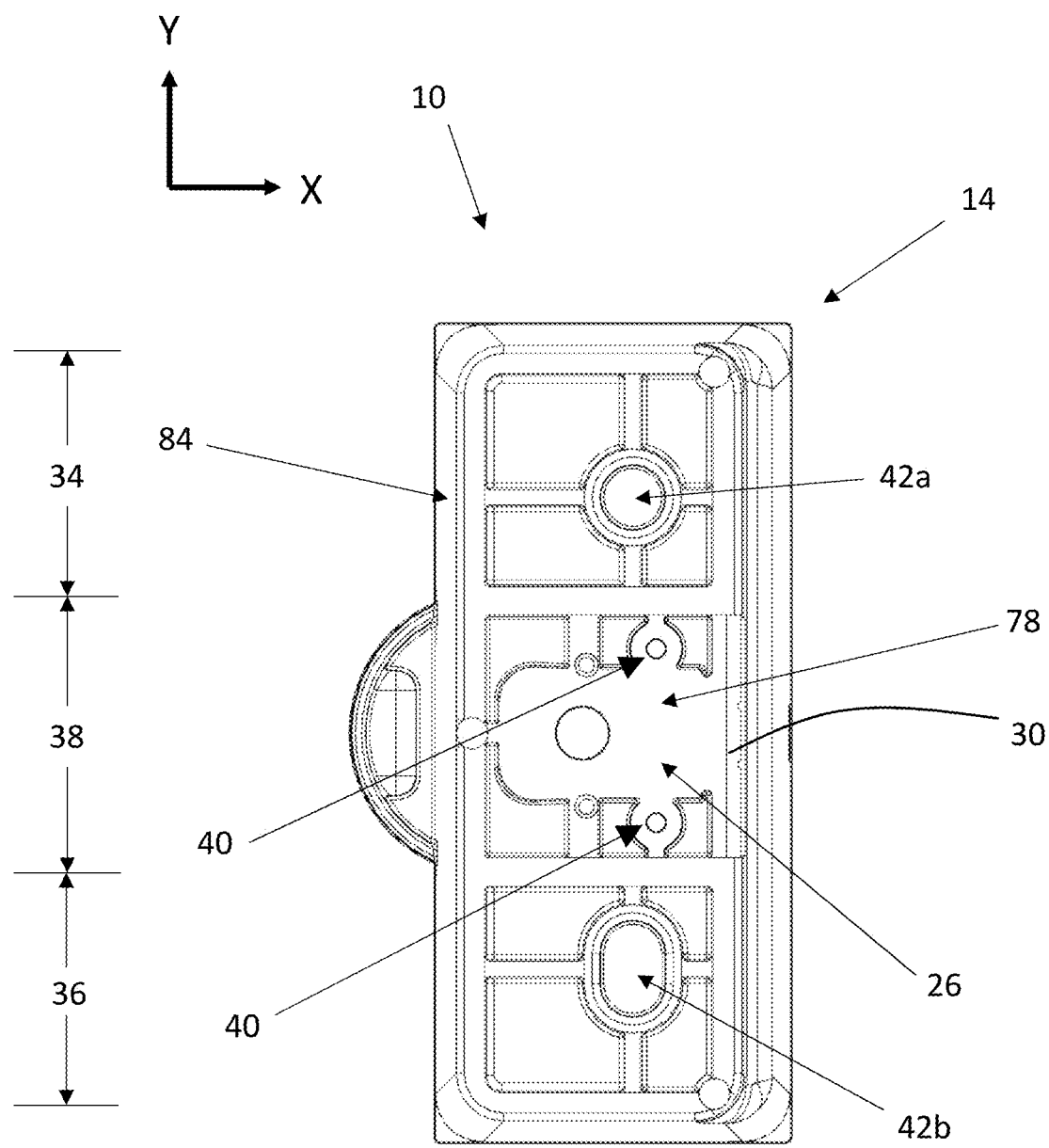
FIG. 4 is a bottom, plan view of the microfluidic cartridge of FIG. 1.

The first face 26 may include one or more elements to provide alignment and a robust electrical connection for connecting a microfluidic cartridge 10 with a microfluidic device. With reference to FIGS. 3 and 4, the first face 26 may be defined by a first end portion 34, a second end portion 36, and a central portion 38 that separates the first and second end portions 34 and 36, respectively. The first face 26 may have one or more elements formed into the first face 26. For example, the first face 26 may include one or more openings, such as one or more minor openings 40 and one or more major openings 42. As will be discussed in more detail below, the positioning of the minor openings 40 may be aligned with the positioning of the electronic components, such as the electrical circuit, in order to help maintain proper alignment of the electrical components. If one or more major openings 42 are present, the major openings may be spaced in different portions of the first face 26. For example, one major opening 42 may be disposed in the first end portion 34 and/or one major opening 42 may be disposed in the second end portion 36. Major openings 42 may also be placed in the central region, depending on placement of the electrical circuit.

Figure 7:
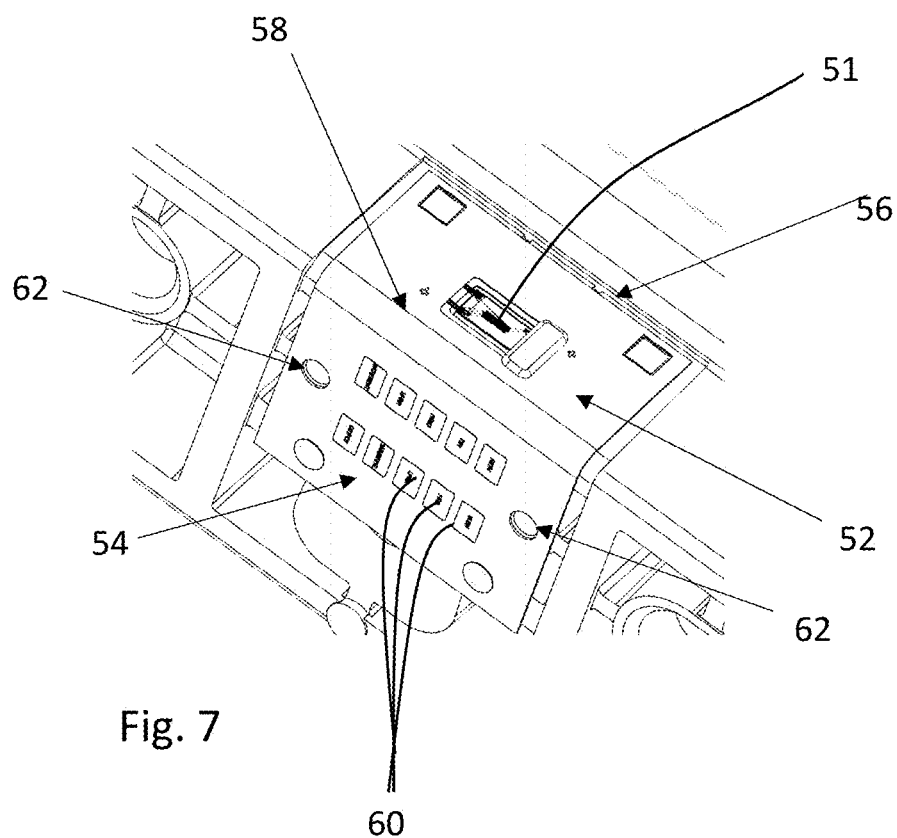
FIG. 7 is a magnified view of portion 7 of FIG. 6.

With reference to FIGS. 6 and 7, the microfluidic cartridge 10 comprises an electrical circuit 52. The electrical circuit 52 may be in the form of a flexible circuit, semi-flexible circuit having rigid and flexible portions, and rigid circuit boards. The electrical circuit 52 may include a first end portion 54, a second end portion 56, and a central portion 58 separating the first and second end portions 54 and 56, respectively. The first end portion 54 of the electrical circuit 52 may be disposed on the first face 26 of the microfluidic cartridge 10, the second end portion 56 of the electrical circuit 52 may be disposed on the second face 28 of the microfluidic cartridge 10, and the central portion 58 of the electrical circuit 52 may span the first and second faces 26 and 28, respectively, of the microfluidic cartridge 10. The first end portion 54 of the electrical circuit 52 may include electrical contacts 60 for connecting with the electrical contacts of the housing of a microfluidic delivery device. The second end portion 56 of the electrical circuit 52 may be in electrical communication with the microfluidic die 51.

The first end portion 54 of the electrical circuit 52 may include one or more circuit openings 62. The circuit openings 62 in the first end portion 54 of the electrical circuit 52 may align with the minor openings 40 in the first face 26 of the microfluidic cartridge 10. Like the minor openings 40 in the first face 26, the circuit openings 62 in the first end portion 54 of the electrical circuit 52 may be relatively small, fine-tuning alignment openings. The minor openings 40 may have a smaller open area than the open area of the circuit openings 62 to allow for minor misalignment of the electrical circuit 52 relative to the minor openings 40.

With reference to FIGS. 4 and 6-7, minor openings 40 in the first face 26 may always align with circuit openings 62 in the electrical circuit 52, or minor openings 40 in the first face 26 may be disposed away from the electrical circuit 52 to provide additional fine-tune alignment of the microfluidic cartridge 10.

The circuit openings 62 may be present in configurations where no minor openings exist.

Placing circuit openings 62 directly on the electrical circuit 52 may provide for a robust electrical connection between the microfluidic cartridge 10 and a microfluidic delivery device while the microfluidic cartridge 10 is connected with the microfluidic delivery device. If more than one circuit opening 62 is present in the first end portion 54 of the electrical circuit 52, at least two circuit openings 62 may be disposed on opposite sides of the electrical contacts 60 or may be separated by the electrical contacts 60. Placing the circuit openings 62 on opposite sides of the electrical contacts 60 of the electrical circuit 52 may provide a robust electrical connection between the microfluidic cartridge 10 and a microfluidic device. Having two or more circuit openings 62 on the electrical circuit 52 may limit the microfluidic cartridge from moving in the X and Y-directions.

A first face 26 comprising at least two minor openings 40, or at least one minor opening 40 and at least one major opening 42, or at least two minor openings 40 in combination with at least one major opening 42 may prevent movement of the microfluidic cartridge 10 relative to a housing of a microfluidic delivery device in the X and Y-directions. By placing openings, major and/or minor first face 42 and/or 40, respectively, in each of the first end portion 34 and second end portion 36 of the first face 26, greater stability can be achieved than if openings are only in one of the first and second end portions 34 and 36, respectively.

With reference to FIGS. 10-13, a microfluidic cartridge 10 may be configured to be releasably connectable with a microfluidic delivery device 44. The microfluidic delivery device 44 may comprise a housing 46 and a power source 48. The housing 46 may include a receptacle 64 having an opening 66 for receiving the microfluidic cartridge 10. The receptacle 64 may receive a portion of the microfluidic cartridge 10 or the microfluidic cartridge 10 may be completely disposed within the receptacle 64. The receptacle 64 of the housing 46 may include electrical contacts 68 that are configured to electrically connect with the electrical contacts 60 of the microfluidic cartridge 10. As will be discussed in more detail below, the electrical contacts 68 may be spring-loaded such that they make a robust electrical connection with the electrical contacts 60 on the microfluidic cartridge 10.

The receptacle 64 may include one or more minor guideposts 70 configured be received by the circuit openings 62 and/or the minor openings 40 of the microfluidic cartridge 10. The receptacle 64 may include one or more major guideposts 72 configured to be received by the major openings 42 of the microfluidic cartridge 10. The minor guideposts 70 are sized and shaped to fit within the circuit openings 62 and/or minor openings 40 and to provide minimal clearance between to the minor guide posts 70 and the circuit openings 62 and/or the minor openings 40. The major guideposts 72 are sized and shaped to fit within the major openings 42 and provide minimal clearance between to the major guide posts 72 and the major openings 42.

The housing 46 may include a faceplate 47 disposed on a front side of the housing 46. The housing 46 may also include a fluid outlet 74 for releasing the fluid composition from the microfluidic cartridge 10 into the air. The housing 46 may include a first air outlet 76 for directing air toward the dispensed fluid composition upward and/or outward into the surrounding space. The fluid outlet 74 and the first air outlet 76 may be disposed in the faceplate 47.

With reference to FIGS. 4-7 and 13, the minor openings 40, circuit openings 62, and/or major openings 42 may be used to align and limit movement of the microfluidic cartridge 10 relative to the housing of a microfluidic delivery device 44. The minor openings 40 and major openings 42 may have different open areas. Major openings 42 may have a larger open area than the open area of the minor openings 40 and may be used for major alignment of the microfluidic cartridge 10 with one or more major guideposts 72 in the housing 46 of a microfluidic delivery device 44. Minor openings 40 and/or circuit openings 62 in the microfluidic cartridge 10 may be used for minor or fine-tuning alignment of the microfluidic cartridge 10 with one or more minor guideposts 70 in the housing 46. Providing fine-tuning alignment of the microfluidic cartridge 10 may provide for a robust electrical connection between the housing 46 and the microfluidic cartridge 10. Major alignment may assist a user with inserting and aligning the microfluidic cartridge 10 in the proper orientation with the housing 46. Major openings 42 may prevent a user from connecting the microfluidic cartridge 10 with the housing 46 in a way that fails to make proper electrical connection with the housing 46 or fails to align the microfluidic die 51 in the proper firing direction. Mating the minor openings 40 and/or circuit openings 62 of the microfluidic cartridge 10 with minor guideposts 70 of the housing 46 may prevent movement of the microfluidic cartridge 10 relative to the housing 46 of the microfluidic delivery device 44 in the X and Y-directions. Mating the major openings 42 of the microfluidic cartridge 10 with major guideposts 72 of the housing 46 may limit movement of the microfluidic cartridge 10 relative to the housing 46 of the microfluidic delivery device 44 in the X and Y-directions.

The major openings 42 may be able to absorb any force caused by movement of the microfluidic cartridge 10 in order to protect the minor guidepost(s) 70 or electrical circuit 52 from experiencing excessive force caused by movement of the microfluidic cartridge 10. Thus, by having at least one minor opening 40 and at least one major opening 42, the microfluidic cartridge 10 may provide for simple alignment by a user, robust electrical connections with a housing, and force distribution that protects the electrical circuit 52 and the minor guidepost(s) 70 from movement of the microfluidic cartridge 10.

With reference to FIG. 6, circuit openings 62 in the electrical circuit 52 may be present when minor openings are not present in the first face 26. In such a configuration, the minor guideposts 70 are only received by the circuit openings 62 in the electrical circuit 52.

The major openings 42 may be configured to have the same shape as each other major opening 42 or may be configured such that at least one major 42 opening has a different shape.

For example, with reference to FIG. 4, a first major opening 42a may have a first shape and a second major opening 42b may have a second shape that is different from the first shape. For illustrative purposes only, the first major opening 42a may be circular and the second opening 42b may be obround or stadium shape. By having differently shaped major openings 42, the microfluidic cartridge 10 may only connect with the housing 46 of the microfluidic delivery device 44 in one orientation, which provides proper electrical connection and functioning of the microfluidic die 51. The different shapes may be selected such that the for the major openings 42 so that the major guideposts 72 will only fit into one of the major openings 42. For example, with reference to FIGS. 4 and 13, the circular major guidepost 72 may only fit into the circular major opening 42 and the obround major guidepost 72 may only fit into the obround major opening 42.

In addition to or in alternative from the major openings 42, the minor openings 40 and/or the circuit openings 62 may also be configured to have the same shape as each other minor opening 40 or may be configured such that at least one minor opening 40 has a different shape.

With reference to FIGS. 3 and 6-7, the first and/or second faces 26 and/or 28, respectively, may include an inset region 78 at the location where the electrical circuit 52 is joined with the microfluidic cartridge 10. The inset region 78 may be sized such that the electrical circuit 52 is able to fit within the inset region 78. With reference to FIGS. 6-7, the inset region 78 may be sized such that when the electrical circuit 52 is joined with the microfluidic cartridge 10, the electrical circuit 52 is flush with the surrounding surfaces of the first and second end portions 34 and 36, respectively, of the first face 26.

For illustrative purposes only, the electrical circuit shown in FIGS. 4 and 7 is disposed in the central region 38 of the first face 26 and the central region 38 of the first face 26 is recessed in the Z-direction relative to the first and second end portions 34 and 36, respectively. As such, the electrical circuit 52 sits relatively flush with the Z-directional height of the first and second end portions 34 and 36, respectively.

The minor openings 40 may be inset on the first face 26 in the Z-direction relative to the major openings 42 such that the microfluidic cartridge 10 aligns first with the major guideposts 72 to ensure the microfluidic cartridge 10 is properly oriented. Once the major openings 42 begin to receive the major guideposts 72, then the circuit openings 62 and/or the minor openings 40 can receive the minor guideposts 70 for fine-tune, precision alignment of the electrical contacts 60 on the microfluidic cartridge 10 and electrical contacts 68 on the housing 46. Another configuration that would achieve a similar result would include having the major openings 42 and the minor openings 40 at the same relative Z-directional height on the first face 26, but having the major guideposts 72 on the housing 46 extend further than the minor guideposts 70 such that the major guideposts 72 will begin to connect with the major openings 42 before the minor guideposts 70 begin to connect with the minor openings 40 as the microfluidic cartridge 10 is connected with the housing. Or, the major and minor openings 40 and 42 may be disposed at the same relative height in the Z-direction on the first face 26 and the major and minor guideposts 70 and 72 may simultaneously connect with the major and minor openings 40 and 42 on the first face 26.

The microfluidic die 51 may be disposed on the microfluidic cartridge 10 such that it is protected from being touched or hit by a user, a housing of a microfluidic device, or any other surface or object that the microfluidic cartridge 10 may contact. For example, with reference to FIGS. 3 and 5, the second face 28 of the microfluidic cartridge 10 may be defined by a second face outermost point 80 in the X-direction that extends furthest away from the X-axis from any other point on the second face 28. With reference to FIG. 6, the microfluidic die 51 may be disposed on a region of the second face 28 that is positioned inward in the X-direction from the second face outermost point 80.

Figure 5:
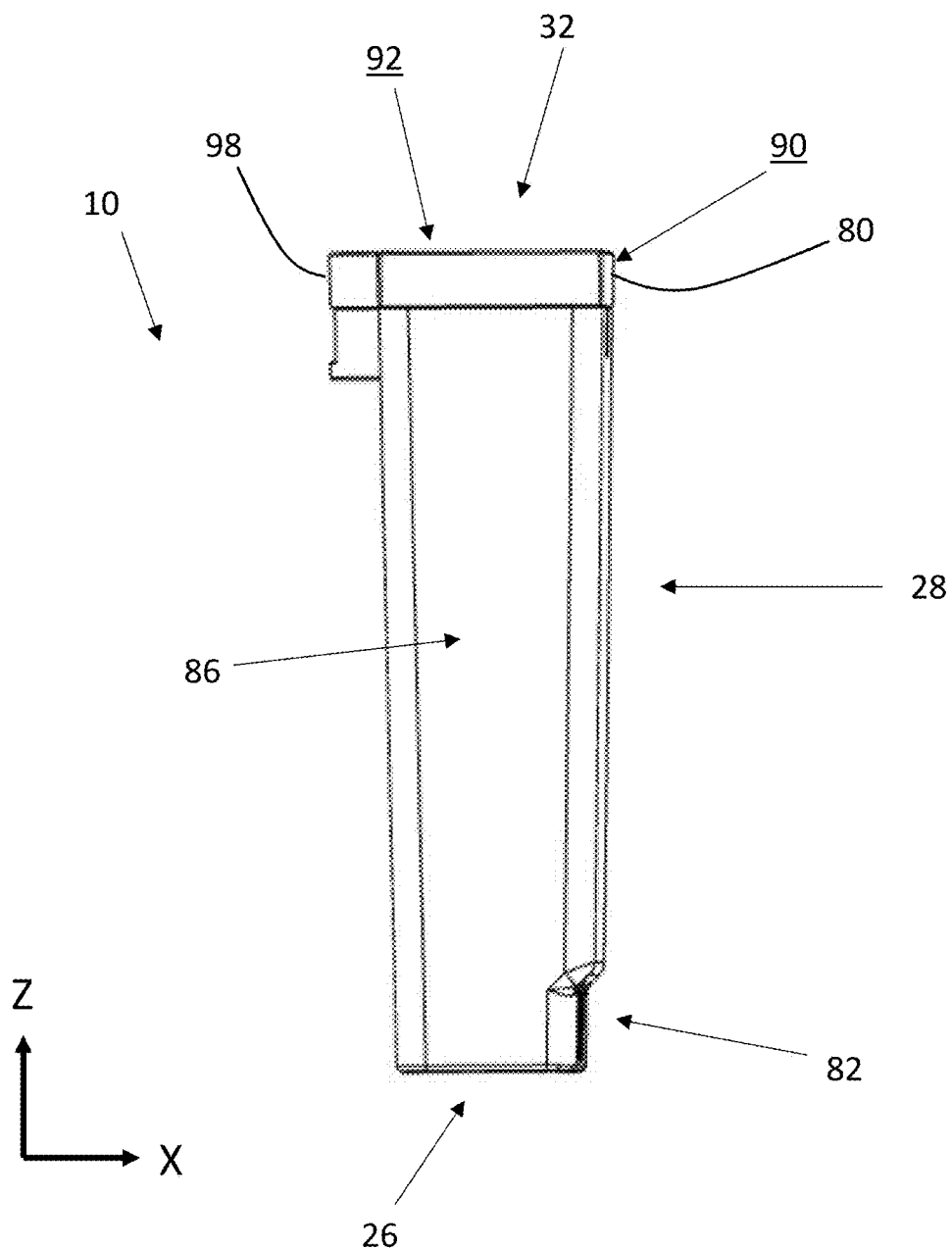
FIG. 5 is a side, elevation view of the microfluidic cartridge of FIG. 1.
Figure 14:
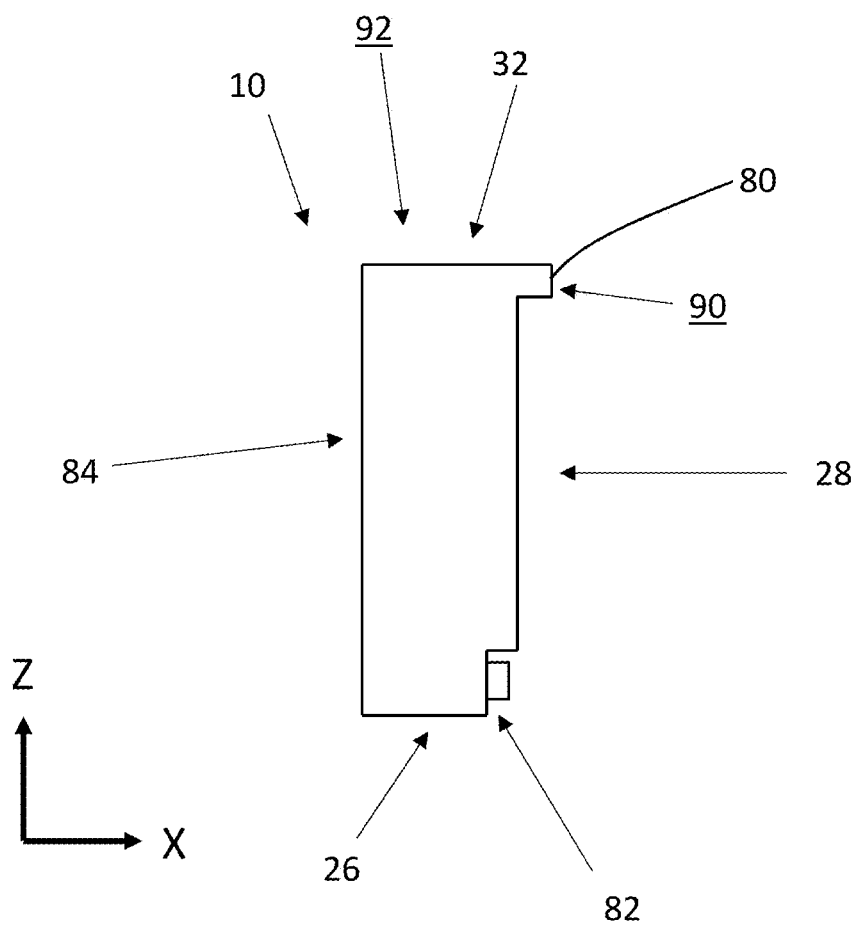
FIG. 14 is a side, elevation view of a microfluidic cartridge.

With reference to FIGS. 5 and 14, the second face outermost point 80 may be located on the lid side surface 90. Or, the second face outermost point 80 may also be disposed on the sidewall 22 of the second face 28.

With reference to FIGS. 3 and 5, in order to position the microfluidic die 51 on an inward surface from the second face outermost point 80 in the X-direction, the second face 28 may include a recessed region 82 that extends from the edge 30 joining the first and second faces 26 and 28, respectively, into the second face 28. The microfluidic die 51 may be disposed on the recessed region 82 in order to protect the microfluidic die 51 from being touched or hit. The recessed region 82 may extend continuously across the entire Y-dimension of the second face 28 from a fifth edge 30e at the fifth face 86 to a sixth edge 30f at the sixth face 88. The recessed region 82 may only extend across a portion of the Y-dimension of the second face 28.

The recessed region 82 may extend to various lengths toward the third face 32 so long as the recessed region 82 is large enough to fit the microfluidic die 51.

As will be discussed in more detail below, having the recessed region 82 extend continuously across the entire Y-dimension of the second face 28 may reduce small turbulent eddies from forming if air from the fan is directed over the microfluidic die 51, resulting in a substantially laminar flow of air exiting the fluid outlet 74. Small turns or changes in direction of air flow can cause the development of turbulent eddies. Therefore, having the recessed region 82 as a single continuous surface area across the Y-dimension may decrease the amount of directional change that the air flow experiences as the air flows over the die and through the fluid outlet 74.

Having the recessed region 78 may also make it possible to mold the base wall 20 and side walls 22 of the reservoir 16 as a single piece. Without a recessed region 78, the fluid channel 18 that extends from the reservoir 16 to the fluid opening 50 may be too long and too difficult to mold as a single piece. By shortening the length of the fluid channel 18 by having a recessed region 78 in the microfluidic cartridge 10, the reservoir 16 may be configured as a single piece of molded material. The lid 24 may be a separate element, or may be a single piece with the reservoir 16.

With reference to FIGS. 3 and 6, the inset region 78 and the recessed region 82 may overlap on the second face 28. For example, the inset region 78 on the second face 28 may be recessed relative to the recessed region 82 such that a surface of the inset region 78 on the second face 28 is disposed inward from the recessed region 82 in the X-direction on the second face 28. In this way, the electrical circuit 52 disposed on the second face 28 sits substantially flush with the surrounding recessed region 82 of the second face 28.

With reference to FIGS. 11, 12, 15, and 16, the microfluidic cartridge 10 may include one or more elements on the third face 32 that assist the user with properly aligning the microfluidic cartridge 10 into the housing. The third face 32 may be a top face is in a user's view as the user inserts the microfluidic cartridge 10 into the housing 46. For example, the microfluidic cartridge 10 may include one or a plurality of projections 94 extending from the third face 32. The projection 94 may align with a recessed region 100 in the receptacle 64 of the housing 46. The projection 94 may extend in the X-direction to a third face outermost point 98. The projection 94 may extend from the third face 32 onto the fourth face 84 such that the projection 94 extends outward in the X-direction on the fourth face 84.

The projection 94 may take various different shapes. For example, the projection 94 may be arcuate, such semicircular, square, rectangular, and the like.

The projection may extend from the third face to an adjacent face. For example, projection 94 may extend outward in the X-direction on the third face 32 and the fourth face 84. Or, the projection 94 may extend outward in the X-direction on the third face 32 and the second face 28. Instead, the projection 94 may be configured to extend in the Y-direction on the third face 32 and the fifth face 86 or the sixth face 88.

Figure 11:
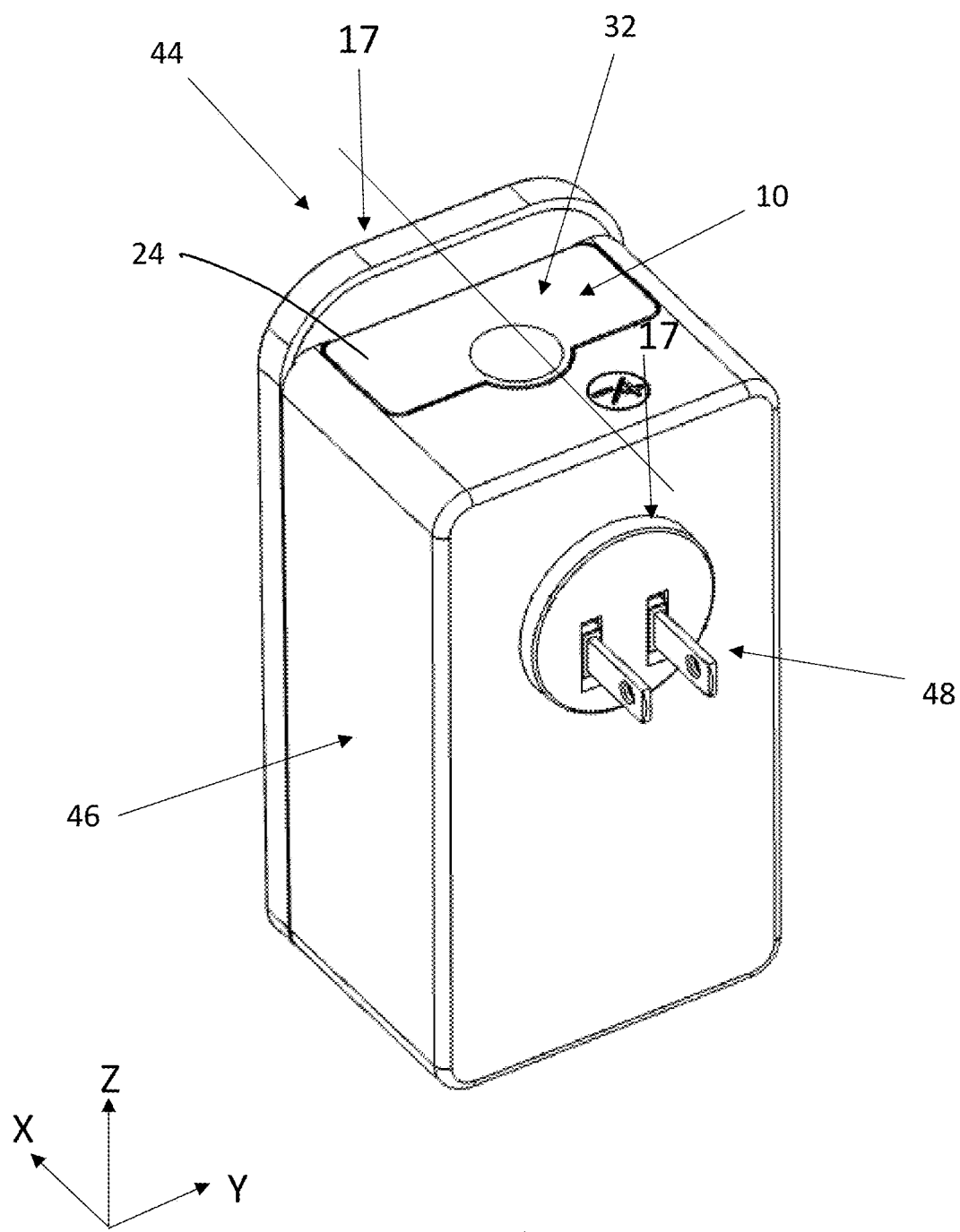
FIG. 11 is an alternative perspective view of the microfluidic delivery device of FIG. 10.
Figure 15:
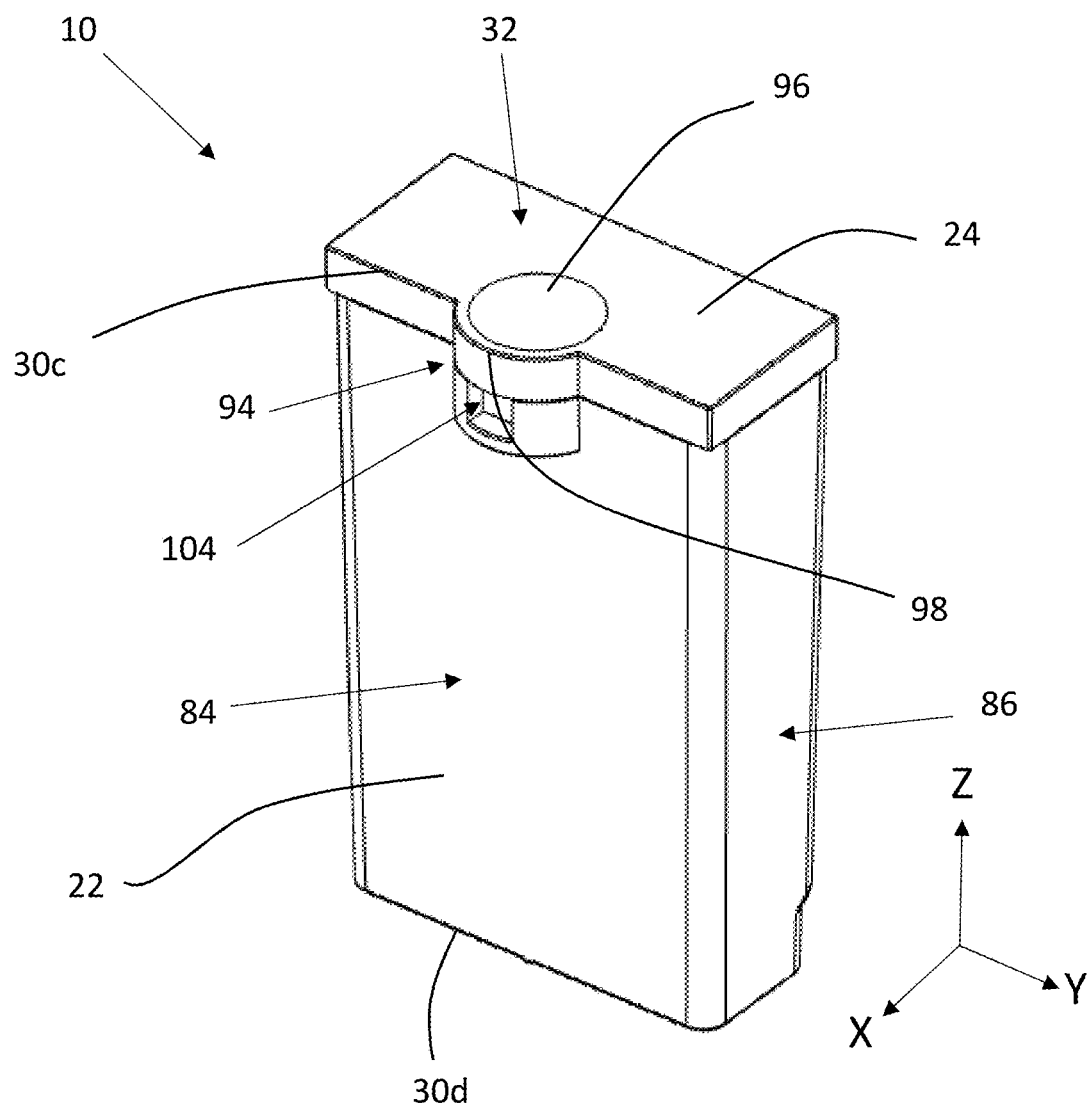
FIG. 15 is an alternative perspective view of the microfluidic cartridge of FIG. 6.
Figure 17:
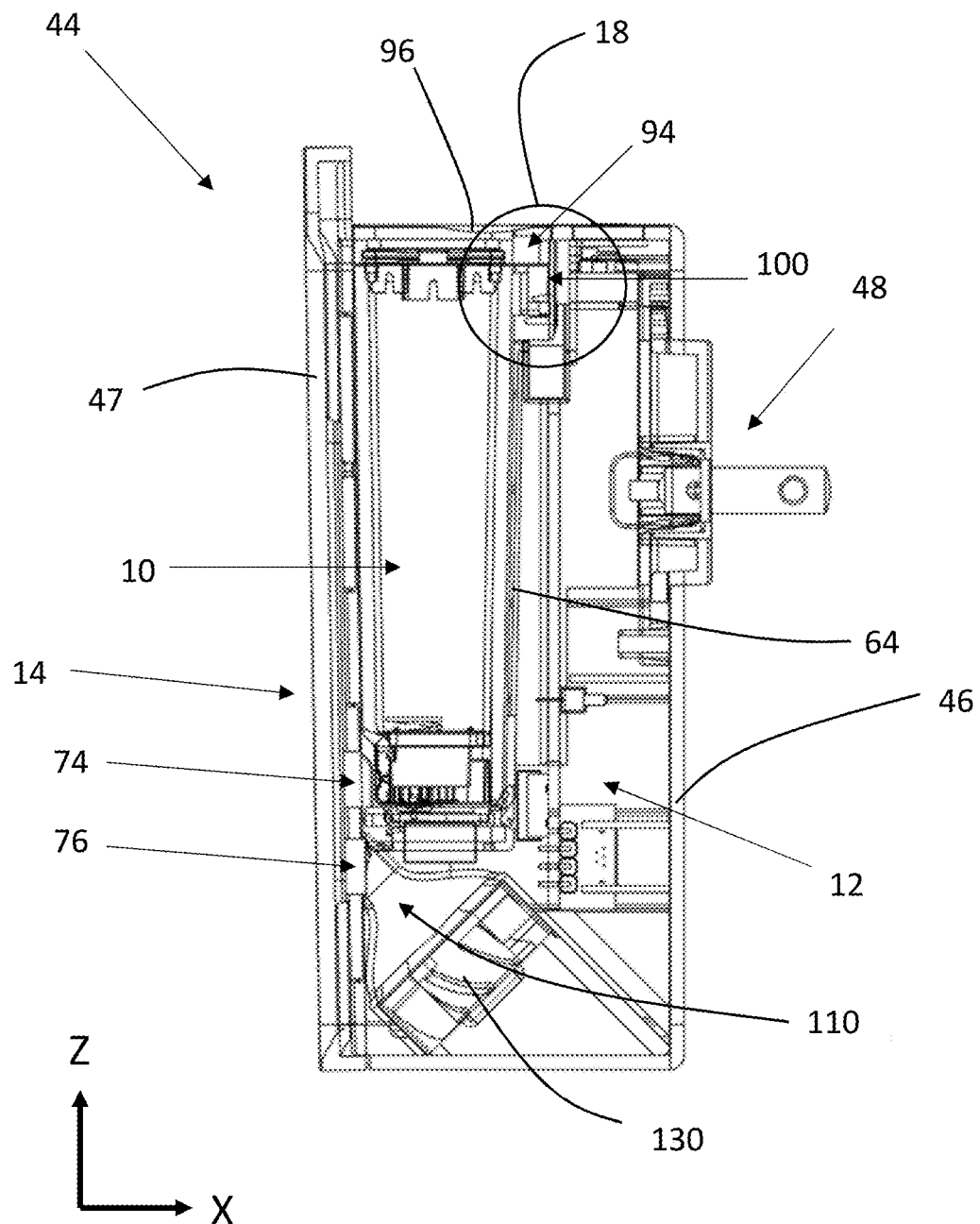
FIG. 17 is a sectional view of FIG. 11 taken along lines 17-17.
Figure 18:
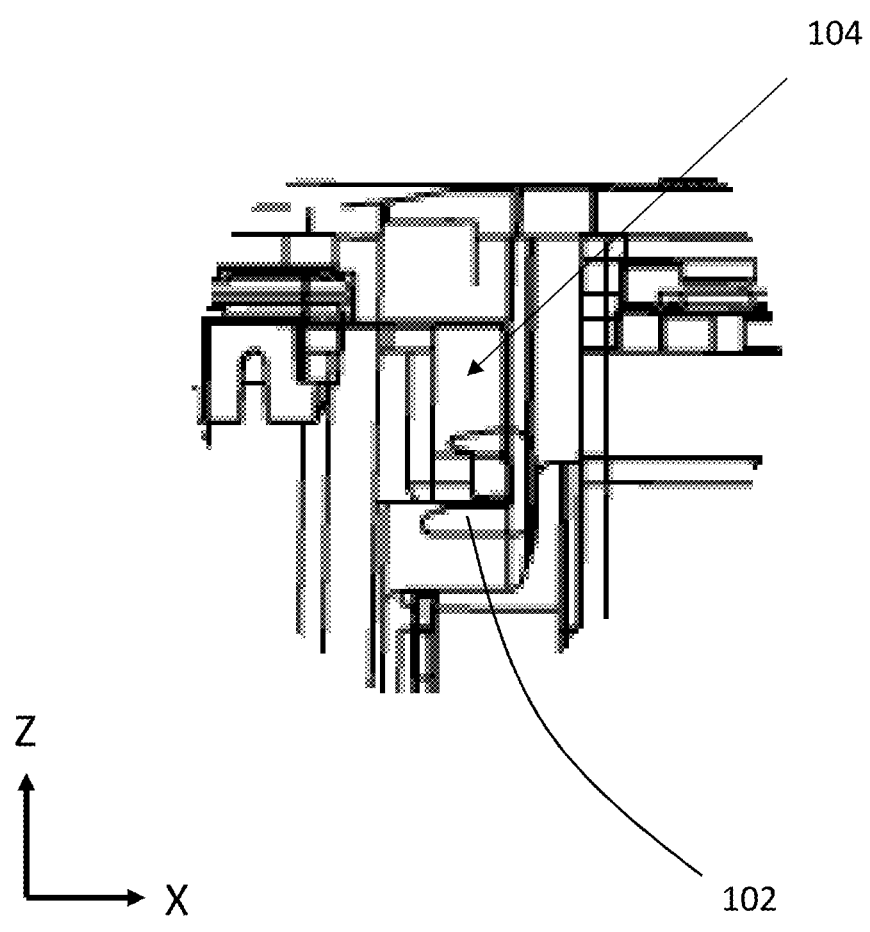
FIG. 18 is an enlarged view of portion 18 of FIG. 17.

With reference to FIGS. 11, 15, and 17, having the projection 94 extend from the third face 32 to the fourth face 84 allows the separation between the face plate 47 of the housing 46 and the reservoir 16 of the microfluidic cartridge 10 to be small. For example, if the projection 94 was disposed from the third face 32 to the second face 28, a larger spacing would have to be set between the face plate 47 and the reservoir 16 of the microfluidic cartridge 10 to make room for the projection 94.

The projection 94 or a portion of the projection 94 may be formed in the lid 24. With reference to FIG. 15, the projection 94 may be formed in the lid 24 and the side wall 22 of the reservoir 16.

Figure 13:
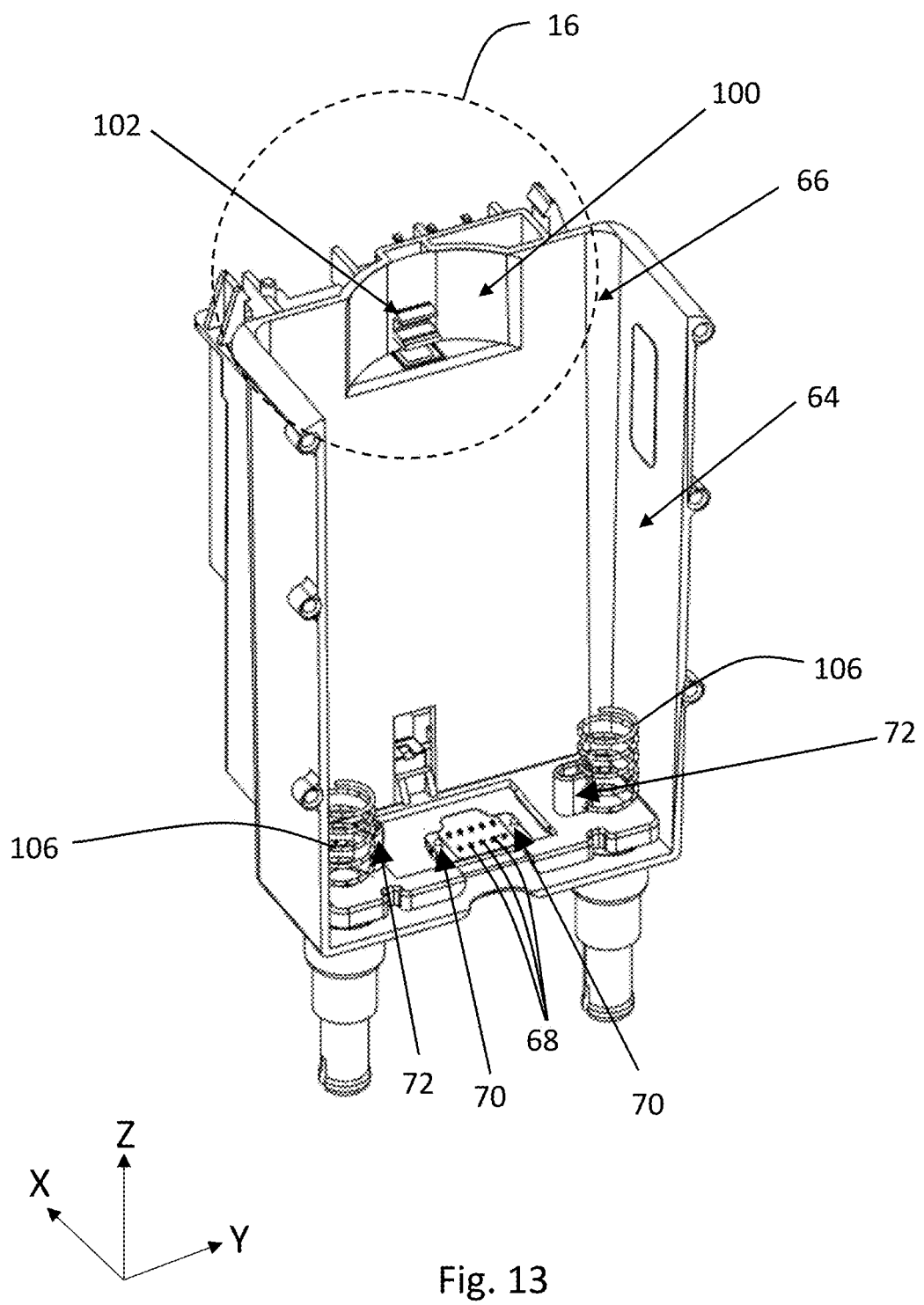
FIG. 13 is a perspective view of a receptacle of a housing of a microfluidic delivery device.
Figure 16:
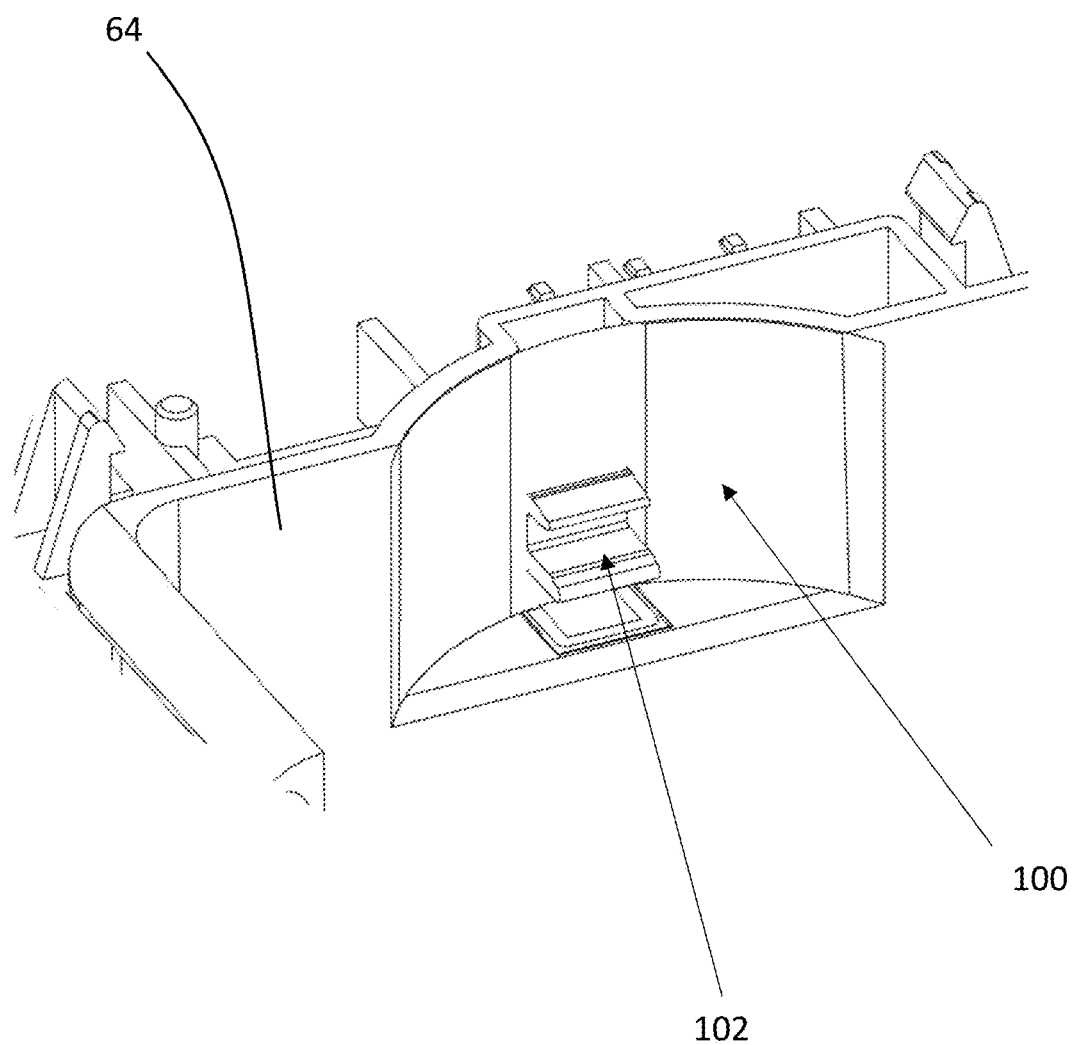
FIG. 16 an enlarged view of portion 16 of FIG. 13.

With reference to FIGS. 13, 15, and 16, the microfluidic cartridge 10 and the housing 46 may include connectors for securing the microfluidic cartridge 10 with the housing 46 when the microfluidic cartridge 10 is connected with the housing 46. For example, the housing 46 may include a first connector 102 and the microfluidic cartridge 10 may include a second connector 104. The first connector 102 may be a male connector and the second connector 104 may be a female connector, or vice versa. The first and second connectors 102 and 104 provide a secure and stable electrical connection in the Z-direction between the housing 46 and the microfluidic cartridge 10.

Figure 12:
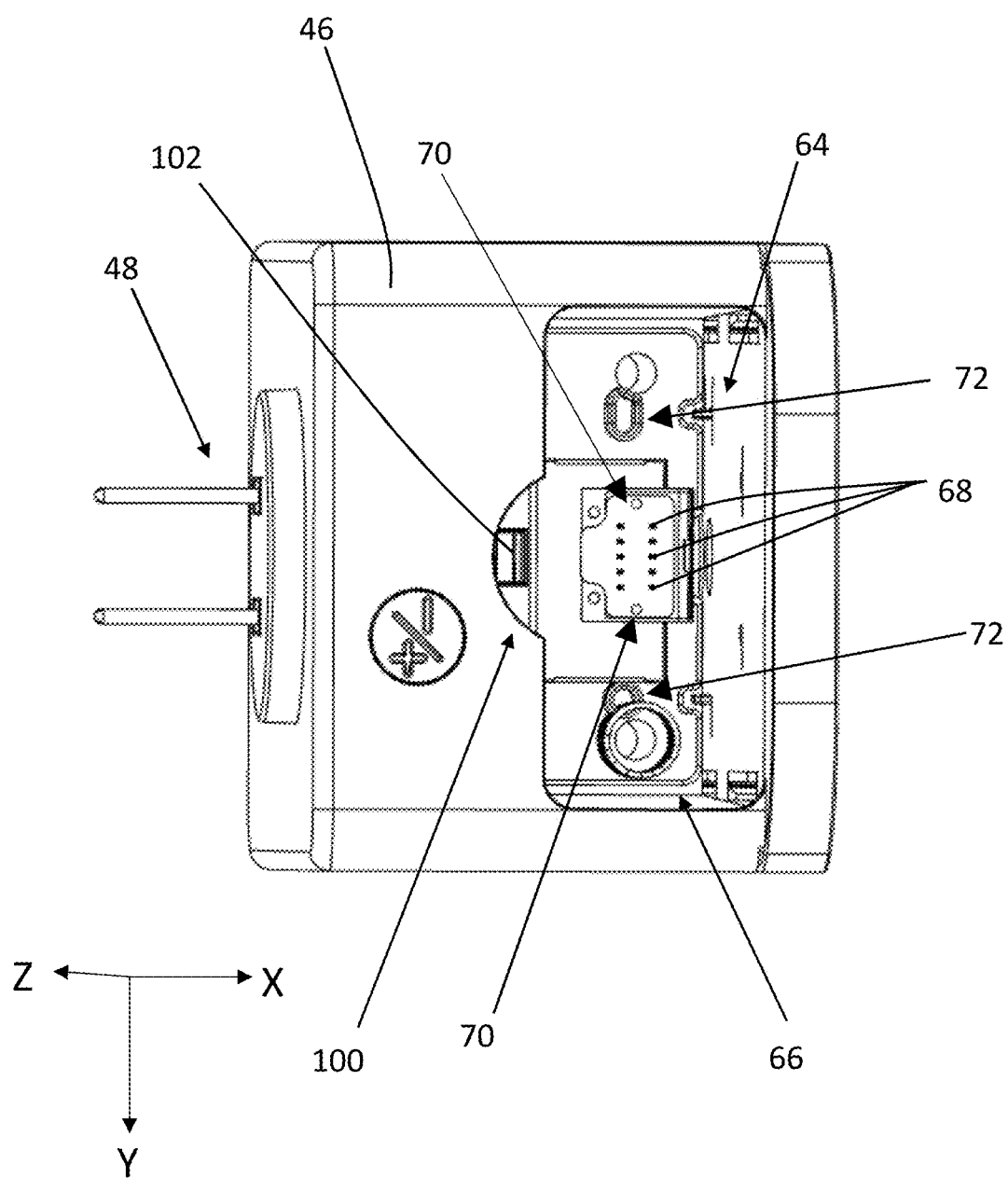
FIG. 12 is a top, plan view of a microfluidic delivery device having a microfluidic cartridge removed to more clearly view elements of an interior of the microfluidic delivery device.

With reference to FIGS. 12, 13, and 15, the second connector 104 may be disposed at the projection 94 in the microfluidic cartridge 10. The first connector 102 in the housing 46 may be disposed at the recessed region 100 where the projection 94 of the microfluidic cartridge 10 mates with the housing 46.

The first connector 102 may be disposed away from the recessed region 100 and/or the second connector 104 may be disposed way from the projection 94.

With reference to FIGS. 4, 7, 15, and 16, a microfluidic cartridge 10 having one or more openings, such as minor openings 40, circuit openings 62, and/or major openings 42 in combination with the second connector 104 provides a microfluidic cartridge 10 that has stability in the X, Y, and Z-directions when secured with a housing 46 of a microfluidic delivery device 44.

With reference to FIG. 13, the microfluidic cartridge 10 may be spring-loaded with the housing 46 so that a user is able to easily remove a microfluidic cartridge 10 from a microfluidic delivery device. For example, the receptacle 64 of the housing 46 may include one or more springs 106 that may be compressed when the second connector 104 of the microfluidic cartridge 10 is joined with the first connector 102 of the housing 46 to secure the microfluidic cartridge 10 with the housing 46. In order to release, the microfluidic cartridge 10, the microfluidic cartridge 10 may be pressed in order to release the connection between the first and second connectors 102 and 104, respectively. Once released, the springs 106 may push the microfluidic cartridge 10 up and out of a microfluidic delivery device.

As previously discussed, the electrical contacts 68 of the housing 46 may be spring-loaded in order to provide a robust electrical connection with the microfluidic cartridge 10. The spring-loaded electrical contacts 68 and the first and second connectors 102 and 104, respectively, may be designed such that a certain level of force is applied by the electrical contacts 60 on the microfluidic cartridge 10 to the electrical contacts 68 on the housing 46. The first and second connectors 102 and 104 may be configured such that the electrical contacts 68 on the housing 46 compress by about 1 mm to about 2 mm.

The microfluidic cartridge may have a release button to release the microfluidic cartridge 10 from the housing 46. Or, the microfluidic cartridge 10 may be pushed toward the housing 46 to engage and/or disengage the microfluidic cartridge 10 from the housing 46. The microfluidic cartridge 10 may engage with a fastener or clip to connect the microfluidic cartridge 10 into the housing 46.

The receptacle 64 may include one or more guiderails for directing the microfluidic cartridge 10 into the receptacle 64.

The microfluidic delivery device may be configured to be compact and easily portable. In such case, the microfluidic delivery device may be battery operated. The microfluidic delivery device may be capable for use with electrical sources as 9-volt batteries, conventional dry cells such as "A", "AA", "AAA", "C", and "D" cells, button cells, watch batteries, solar cells, as well as rechargeable batteries with recharging base.

The microfluidic delivery device may include a fan for generating air flow to assist with delivering the fluid composition into the air. Any fan may be used that provides the desired air flow velocity, size, and power requirements for the microfluidic delivery device. The fan may be used to push the fluid composition further into the air and/or may be used to direct the fluid composition in a different direction than the fluid composition is dispensed from the microfluidic die. The fan may be disposed in the interior of the housing or at least partially in the interior of the housing, or at the exterior of the housing. The fan may also be used to direct air over the microfluidic die 51 to minimize the amount of fluid composition that is deposited back onto the microfluidic die 51.

With reference to FIG. 17, a fan 130 may be disposed within the interior 12 of the housing 46. The fan may be disposed at various angles, depending on the desired direction for the air flow. FIG. 17 illustrates, for exemplary, non-limiting purposes only, that the fan may be angled upward relative to the X-axis such that the air flow is directed at an upward angle from the X-axis. The fan 130 is in air flow communication with an air flow channel 110 that acts as a passageway for the air flow generated by the fan 130.

Figure 19:
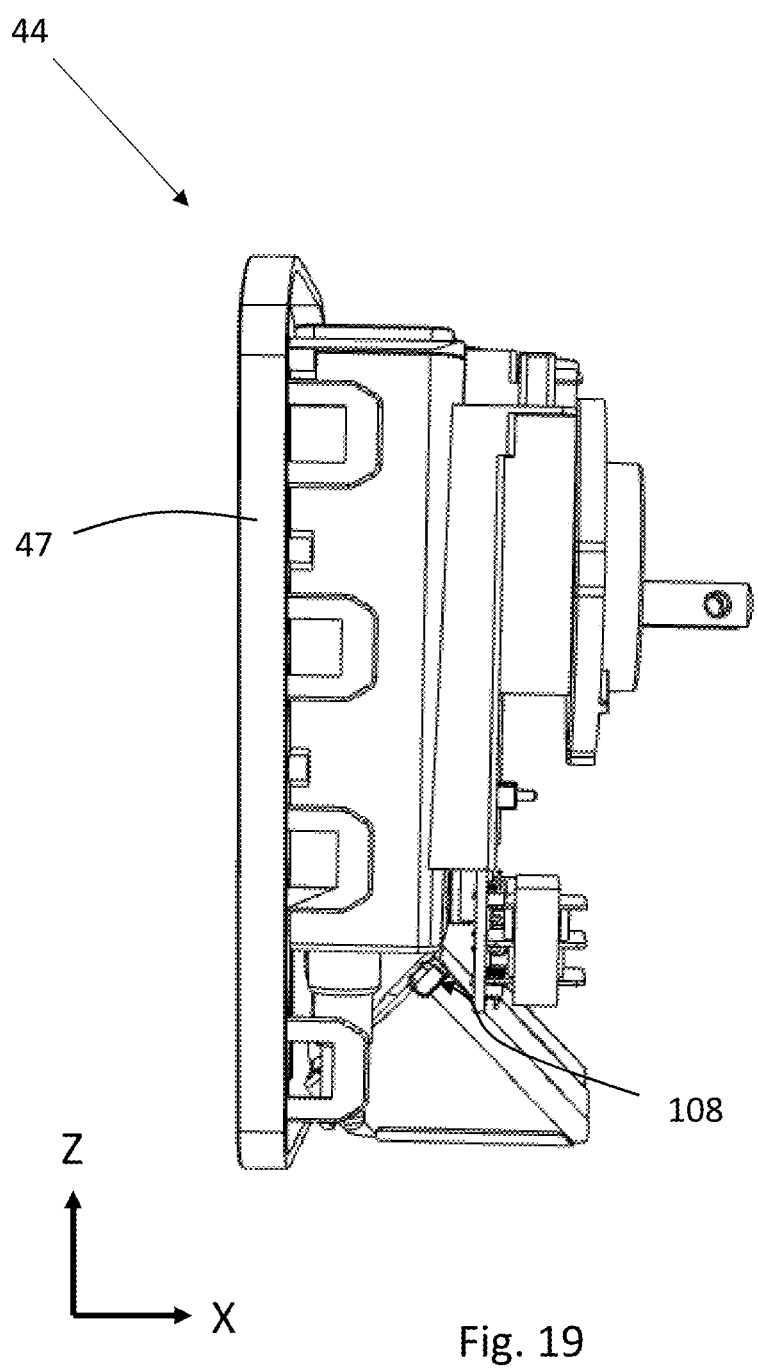
FIG. 19 is a side, elevation view of the microfluidic delivery device of FIG. 11 having a portion of a the housing removed to more clearly illustrate elements at the interior of the microfluidic delivery device.

With reference to FIGS. 17-21, air flow from the fan 130 travels through the air flow channel 110 and to either a first air outlet 76 that opens to the exterior of the microfluidic delivery device or a second air outlet 108 that pressurizes the interior of the microfluidic delivery device. The first air outlet 76 may be disposed in the face plate 47 of the housing 46. With reference to FIG. 19, the second air outlet 108 opens up to the interior 12 of the housing 46. Air flow from the fan 130 then travels in one of two paths, always following the path of least resistance. In order to control the amount of air that exits through the first air outlet 76 or the second air outlet 108, the back pressure at the first air outlet 76 and/or the second air outlet 108 can be designed accordingly. For example, in order to have a greater volume of air exiting the first air outlet 76, the back pressure at the first air outlet 76 may be less than the back pressure at the second air outlet 108. A first portion of the air flow may travel out of the first air outlet 76 to push the fluid composition dispensed from the microfluidic die into the air. A second portion of the air flow may travel through the second air outlet 108 through the interior 12 of the housing 46, over the microfluidic die 51, and out the fluid outlet 74. The second portion of air flow may assist with keeping droplets of fluid composition 21 moving in a substantially laminar flow as the fluid composition 21 exits the fluid outlet 74, and preventing the droplets of fluid composition 21 from depositing back onto the microfluidic die 51 or the surrounding surfaces. The first portion of air flow may assist with pushing the dispensed fluid composition outward and/or upward into the air.

Figure 20:
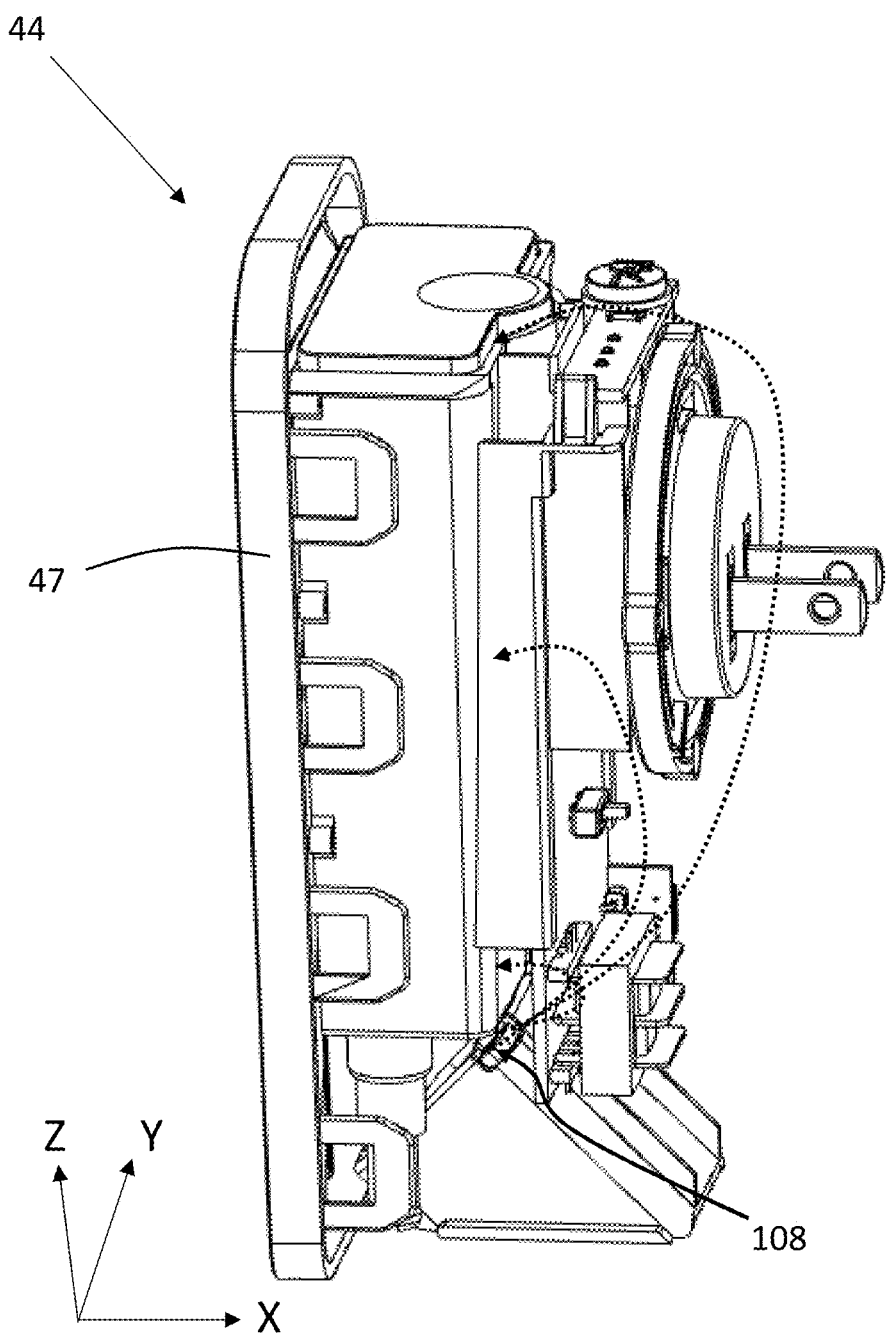
FIG. 20 is an alternative perspective view of FIG. 19 that illustrates a second air outlet.
Figure 21:
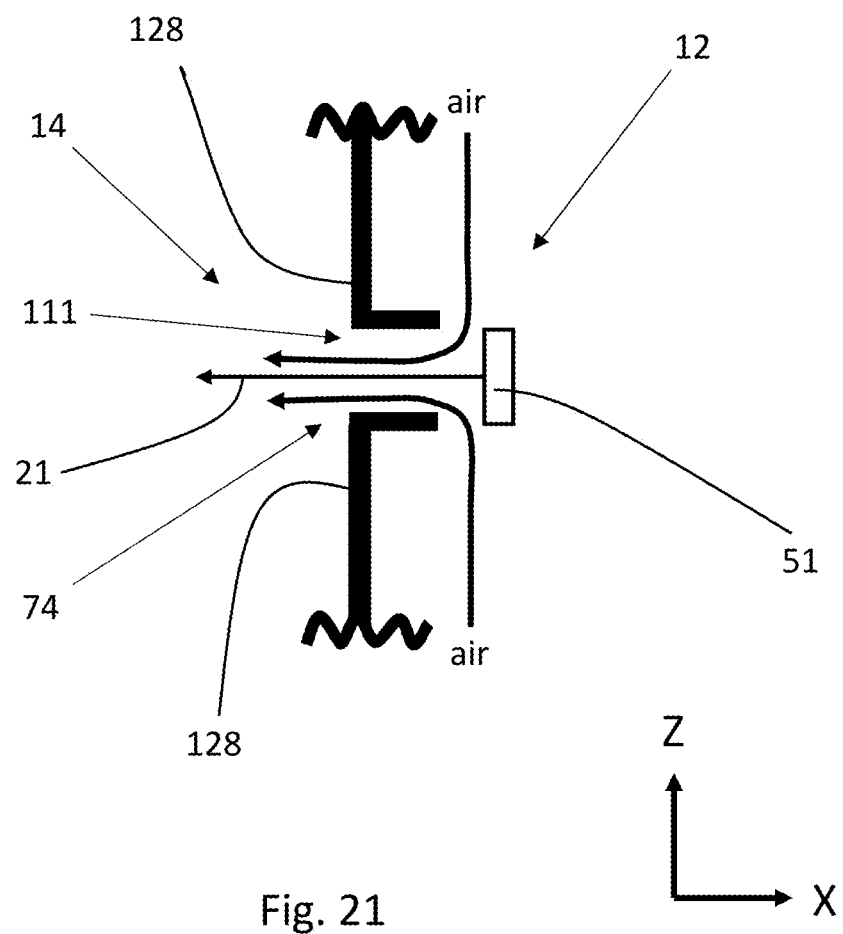
FIG. 21 is a schematic of a side, elevation view of a microfluidic die and a fluid opening in a face plate of a housing of the microfluidic delivery device to illustrate fluid composition being dispensed from the microfluidic die and air flow pushing the fluid composition out of a fluid outlet.

With reference to FIGS. 20 and 21, the second portion of the air flow that travels into the interior 12 of the housing 46 acts to pressurize the interior 12 of the housing 46. The air travels from the second air outlet 108 through the interior 12 and to the fluid outlet 74. The fluid outlet 74 is the highest-pressure opening to the exterior 14 of the housing 46 where air is intended to travel through, and air will travel through any open spaces within the interior 12 of the housing 46 to reach the fluid outlet 74. As such, as shown in FIG. 21, air travels from all directions over the microfluidic die 51 and out the fluid outlet 74.

It may be beneficial to keep the volume of air flow mixing with the fluid composition in the interior 12 of the housing 46 to a minimum because turbulent eddies can form that can impact the ability of the fluid composition to exit the housing and disperse into the air with a substantially laminar flow. Having the majority of the air flow exiting a separate air flow outlet and merge with the fluid composition at the exterior 14 of the housing 46 assists with moving the dispensed fluid composition outward, upward and/or away from the microfluidic delivery device. Therefore, the majority of air generated by the fan 130 may exits the first air outlet 76. At least 70%, or at least 75% or at least 80%, or at least 85%, or at least 90% of air generated by the fan exits the first air outlet. The first air outlet 76 may be designed to produce a lower back pressure than the back pressure produced at the second air outlet 108.

With reference to FIG. 21, the housing may include a fluid channel 111 adjoining the fluid outlet 74. Air passing through the fluid channel 111 may help keep the droplets of fluid composition 21 from the microfluidic die 51 to be centered in the fluid outlet 74 with a substantially laminar flow of air. Keeping the droplets of fluid composition centered as they pass through the fluid outlet 74 may prevent the droplets from depositing onto the housing. The fluid channel 111 may be disposed adjacent the microfluidic die 51. A gap 119 may separate the fluid channel 111 and the microfluidic die 51. The gap 119 may separate the fluid channel 111 from the microfluidic die 51 by a length about 0.75 mm to about 5 mm, more preferably about 1.0 mm to about 3 mm from nozzles of the microfluidic die 51. The fluid channel 111 may have a length of about 2 mm to about 6 mm. The lengths of the gap 119 and/or the fluid channel 111 may be measured in the X-direction.

The average air flow velocity, at the point where the fluid composition and air flow converge, may be in the range of about 0.25 meters/second ("m/s") to about 15 m/s. The average air flow may vary depending on the desired impact on the jetted fluid composition. As discussed above, the air flow channel 34, the air outlet 28, and the fan 32 may be designed to produce an average air flow momentum that is greater than the momentum of the fluid composition at the time the air flow and fluid composition converge in order to change the direction of the fluid composition. As used herein, the "average velocity" of the air flow is an average of the velocities across the entire air flow stream since the air flow stream will have lower velocities near the surfaces of the air flow channel and higher velocities in the center of the air flow stream. Likewise, the "average momentum" as used herein is an average of the momentum across the entire air flow stream.

The air flow exiting the fluid outlet 74 may have a velocity of about 0.25 m/s to about 4 m/s and most preferably between 0.5 m/s and 2 m/s. The air flow exiting the first air outlet 76 may have a velocity of about 1 m/s to about 15 m/s and most preferably between 1 m/s and 5 m/s.

The open area, shape, and orientation of the second air outlet 108 may be selected from any size, shape, or orientation, respectively, depending on the desired impact the air flow is to have on the fluid composition.

Fluid Composition

To operate satisfactorily in a microfluidic delivery device, many characteristics of a fluid composition are taken into consideration. Some factors include formulating fluid compositions with viscosities that are optimal to emit from the microfluidic delivery member, formulating fluid compositions with limited amounts or no suspended solids that would clog the microfluidic delivery member, formulating fluid compositions to be sufficiently stable to not dry and clog the microfluidic delivery member, formulating fluid compositions that are not flammable, etc. For adequate dispensing from a microfluidic die, proper atomization and effective delivery of an air freshening or malodor reducing composition may be considered in designing a fluid composition.

The fluid composition may comprise a perfume composition comprising one or more perfume raw materials. Perfume raw materials deliver a hedonic, fragrance benefit. The fluid composition may contain a perfume mixture present in an amount greater than about 50%, by weight of the fluid composition, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%. The fluid composition may consist entirely of the perfume mixture (i.e. 100 wt. %).

The fluid composition may be substantially free of suspended solids or solid particles existing in a mixture wherein particulate matter is dispersed within a liquid matrix. The fluid composition may have less than 5 wt. % of suspended solids, alternatively less than 4 wt. % of suspended solids, alternatively less than 3 wt. % of suspends, alternatively less than 2 wt. % of suspended solids, alternatively less than 1 wt. % of suspended solids, alternatively less than 0.5 wt. % of suspended solids, or free of suspended solids. Suspended solids are distinguishable from dissolved solids that are characteristic of some perfume materials.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A microfluidic delivery device comprising:

a fan;

a housing having an interior and an exterior, the housing further comprising a first air outlet and a fluid outlet, the interior of the housing comprising an air flow channel that extends from the fan to the first air outlet, the first air outlet being open to the exterior of the housing, wherein the air flow channel comprises a second air outlet that is exposed to the interior of the housing and that is in air flow communication with the fluid outlet, wherein the housing further comprising housing electrical contacts in electrical connection with a power source;

a microfluidic cartridge releasably connectable with the housing, the microfluidic cartridge comprising: a first face; a second face;

a reservoir for containing a fluid composition;

an electrical circuit comprising a first end portion and a second end portion, wherein the first end portion of the electrical circuit is disposed on the first face and the second end portion of the electrical circuit is disposed on the second face; and a microfluidic die disposed on the second face, wherein the microfluidic die is in electrical communication with the electrical circuit and in fluid communication with the reservoir, wherein the second air flow outlet is in air flow communication with the microfluidic die, wherein fluid composition dispensed from the microfluidic die exits the housing through the fluid outlet.

2. The microfluidic delivery device of claim 1, wherein air flow from the fan is directed through the first and second air outlets, wherein air flow entering the second air outlet travels adjacent to the microfluidic die and out of the fluid outlet along with the fluid composition.

3. The microfluidic delivery device of claim 1, wherein the housing comprises a fluid channel extending from the fluid outlet toward the microfluidic die.

4. The microfluidic delivery device of claim 1, wherein the air flow exiting the first air outlet travels at an upward angle relative to horizontal.

5. The microfluidic delivery device of claim 1, wherein a majority of the air flow exits the first air outlet.

6. The microfluidic delivery device of claim 1, wherein the fluid composition is dispensed substantially horizontal.

7. The microfluidic delivery device of claim 1, wherein the microfluidic die comprises a semiconductor substrate comprising a plurality of fluid ejection actuators, a fluid flow substrate comprising a fluid supply channel and one or more fluid chambers, wherein each fluid chamber is associated with a fluid ejection actuator, and a nozzle plate comprising one or more nozzles, wherein each nozzle is in fluid communication with a fluid chamber.

8. The microfluidic delivery device of claim 1, wherein the fluid ejection actuators are thermal actuators, and wherein the fluid composition comprises a perfume mixture.

* * * * *